United States Patent [19]
Kriesel

[11] Patent Number: 5,993,425
[45] Date of Patent: Nov. 30, 1999

[54] FLUID DISPENSER WITH RESERVOIR FILL ASSEMBLY

[75] Inventor: Marshall S. Kriesel, St. Paul, Minn.

[73] Assignee: Science Incorporated, Bloomington, Minn.

[21] Appl. No.: 09/060,852

[22] Filed: Apr. 15, 1998

[51] Int. Cl.⁶ ............................................... A61M 37/00
[52] U.S. Cl. ......................................... 604/191; 604/132
[58] Field of Search .................................. 604/132, 191, 604/187

[56] References Cited

U.S. PATENT DOCUMENTS

| | | | |
|---|---|---|---|
| 5,354,278 | 10/1994 | Kriesel | 604/132 |
| 5,478,323 | 12/1995 | Westwood | 604/191 |
| 5,484,415 | 1/1996 | Kriesel | 604/132 |
| 5,584,815 | 12/1996 | Pawelka et al. | 604/191 |
| 5,688,251 | 11/1997 | Chanoch | 604/187 |
| 5,700,244 | 12/1997 | Kriesel | 604/132 |

*Primary Examiner*—Paul J. Hirsch
*Attorney, Agent, or Firm*—James E. Brunton

[57] ABSTRACT

An apparatus for delivering medicaments to a patient which include a fluid dispensing device and a novel cooperating reservoir fill assembly which can be easily and quickly connected to the fluid dispensing device. The fluid dispensing device uniquely includes an elastomeric bladder stored energy type infusion means which can be used for delivering a wide variety of medicaments such as drugs, medicaments, bilogical agents, or other therapeutic agents at a substantially constant rate.

41 Claims, 18 Drawing Sheets

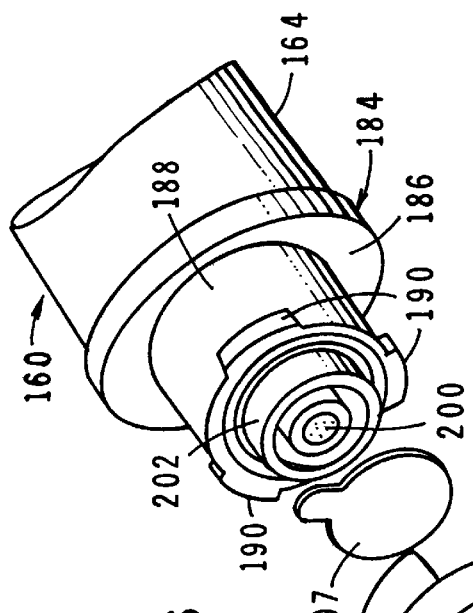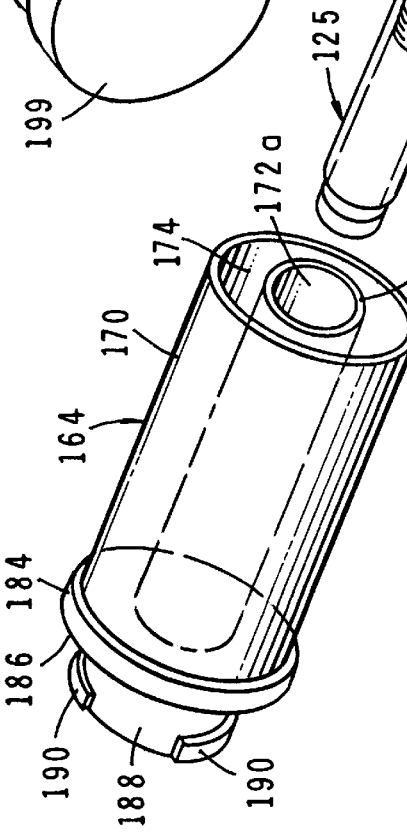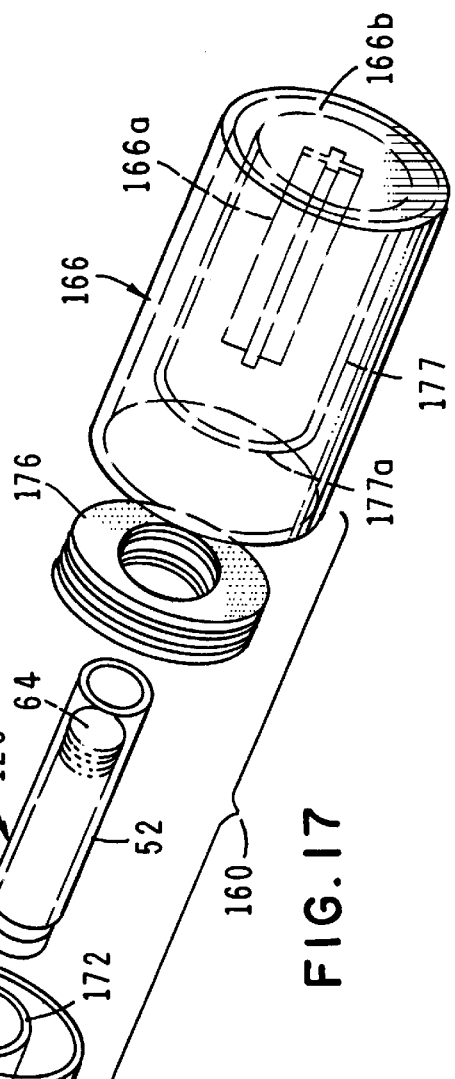

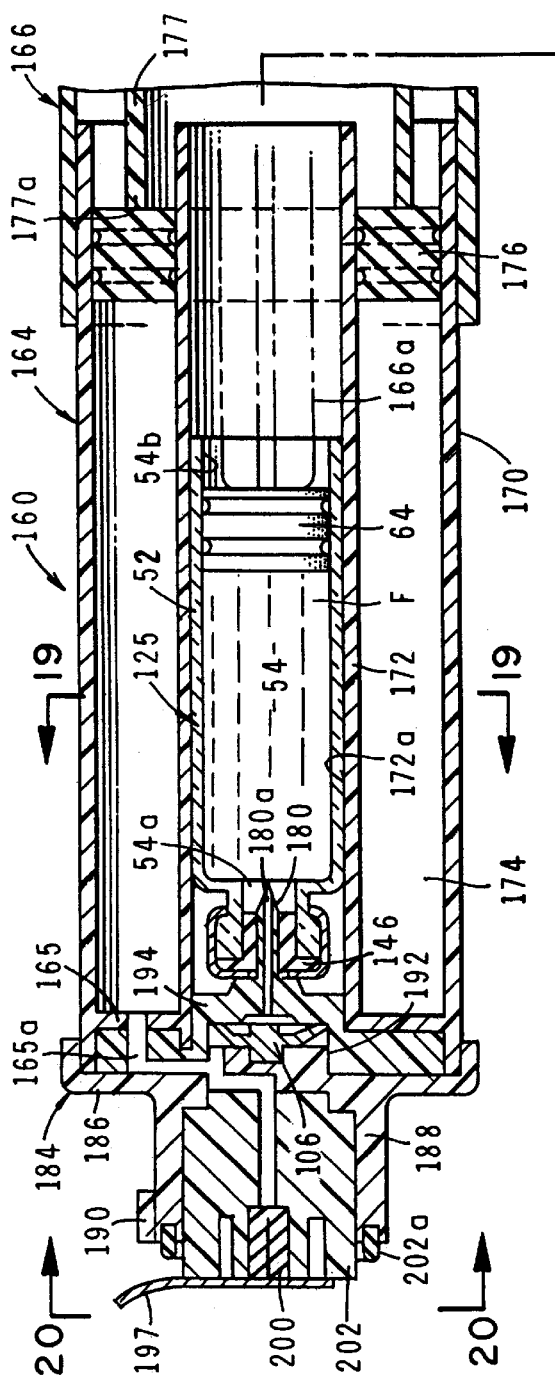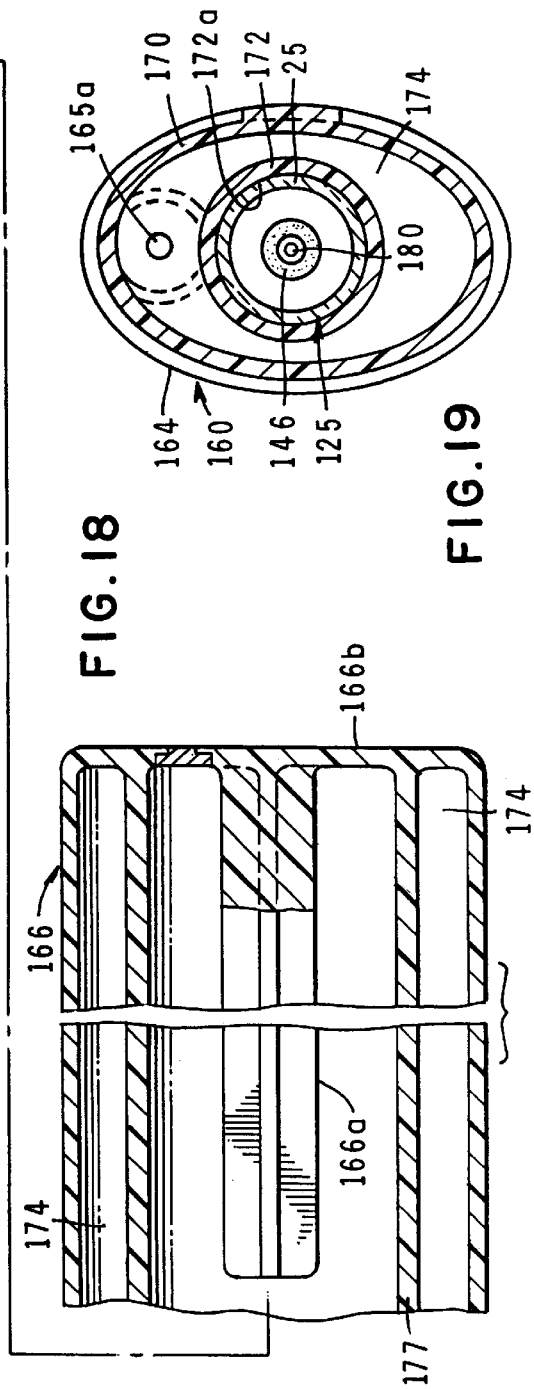
FIG. 18
FIG. 19

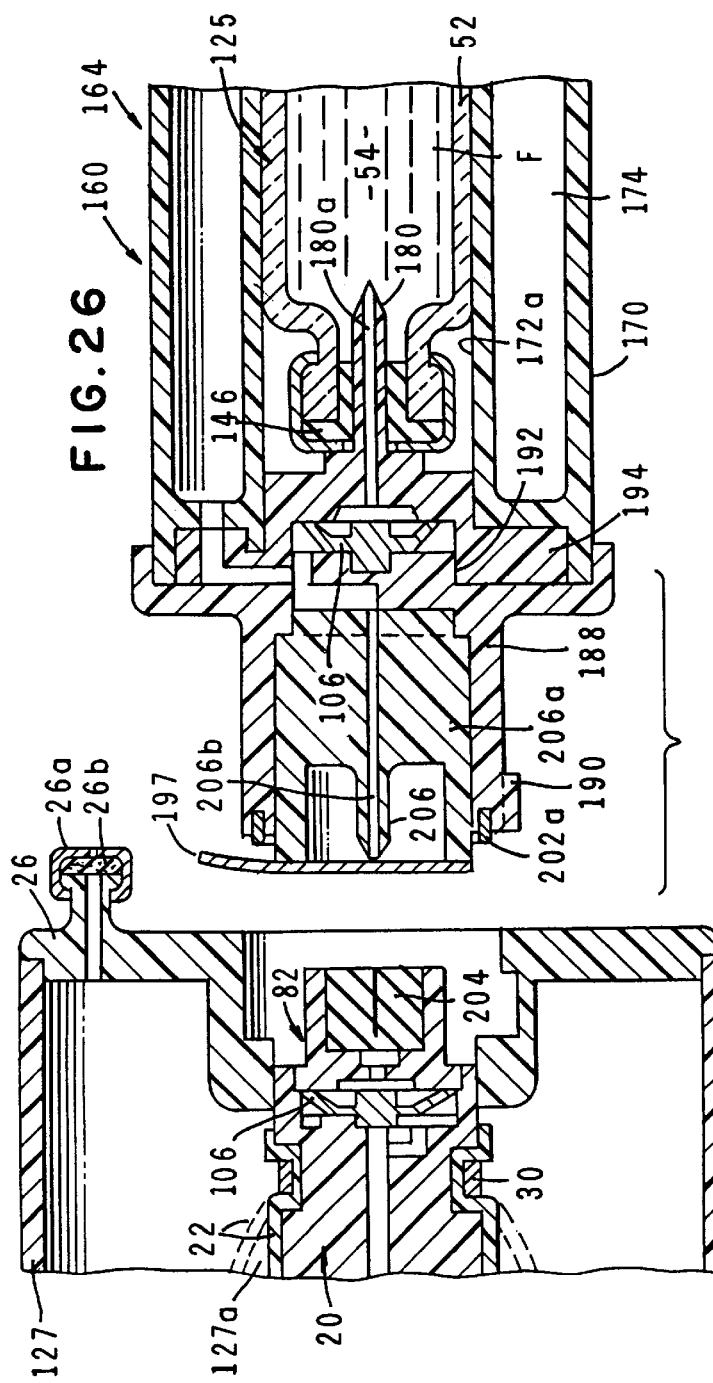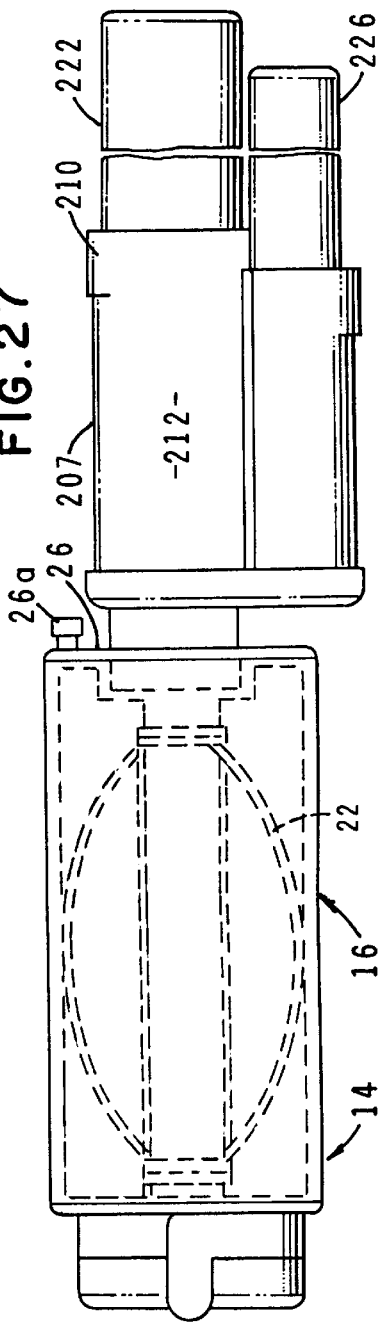

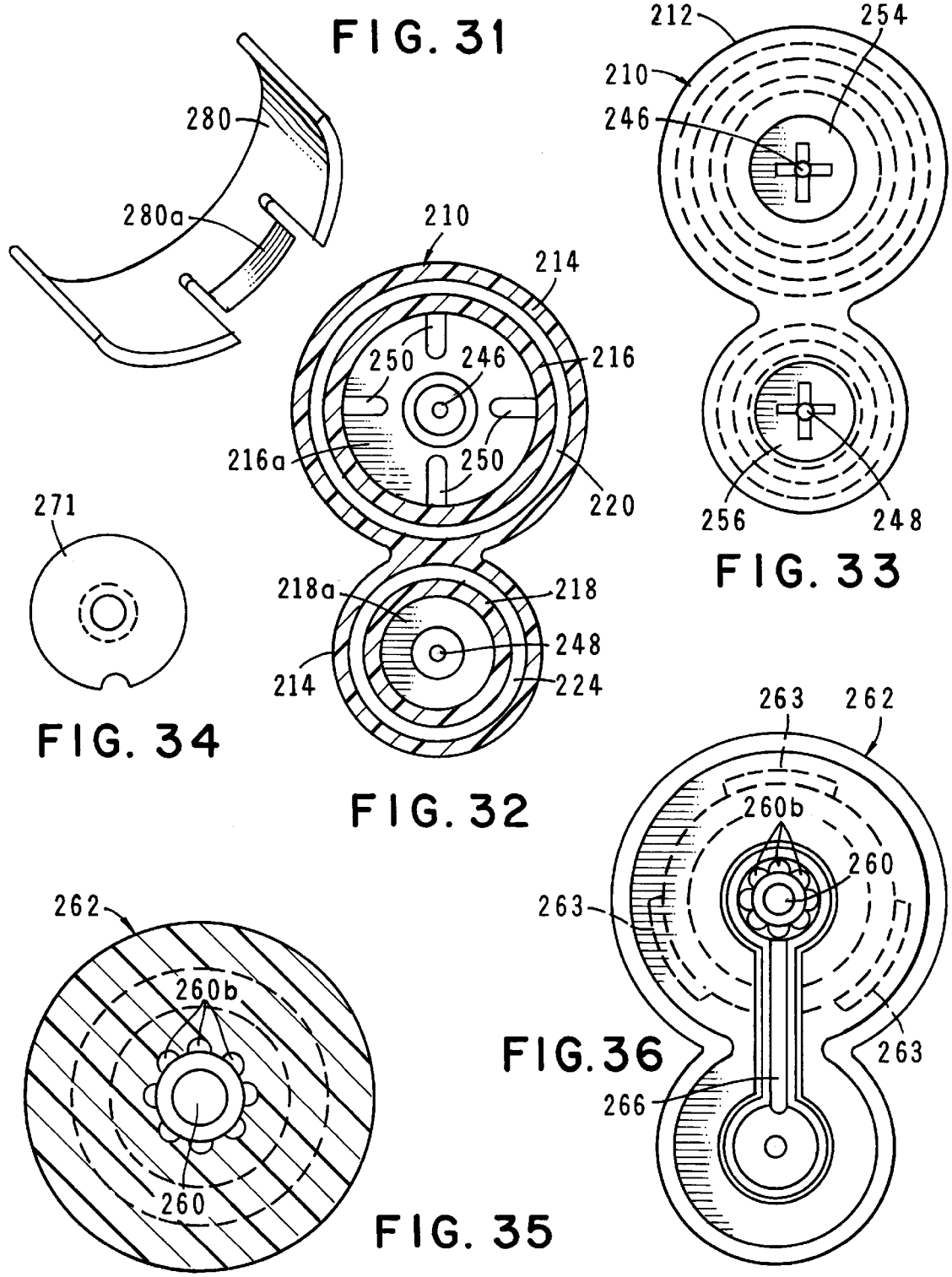

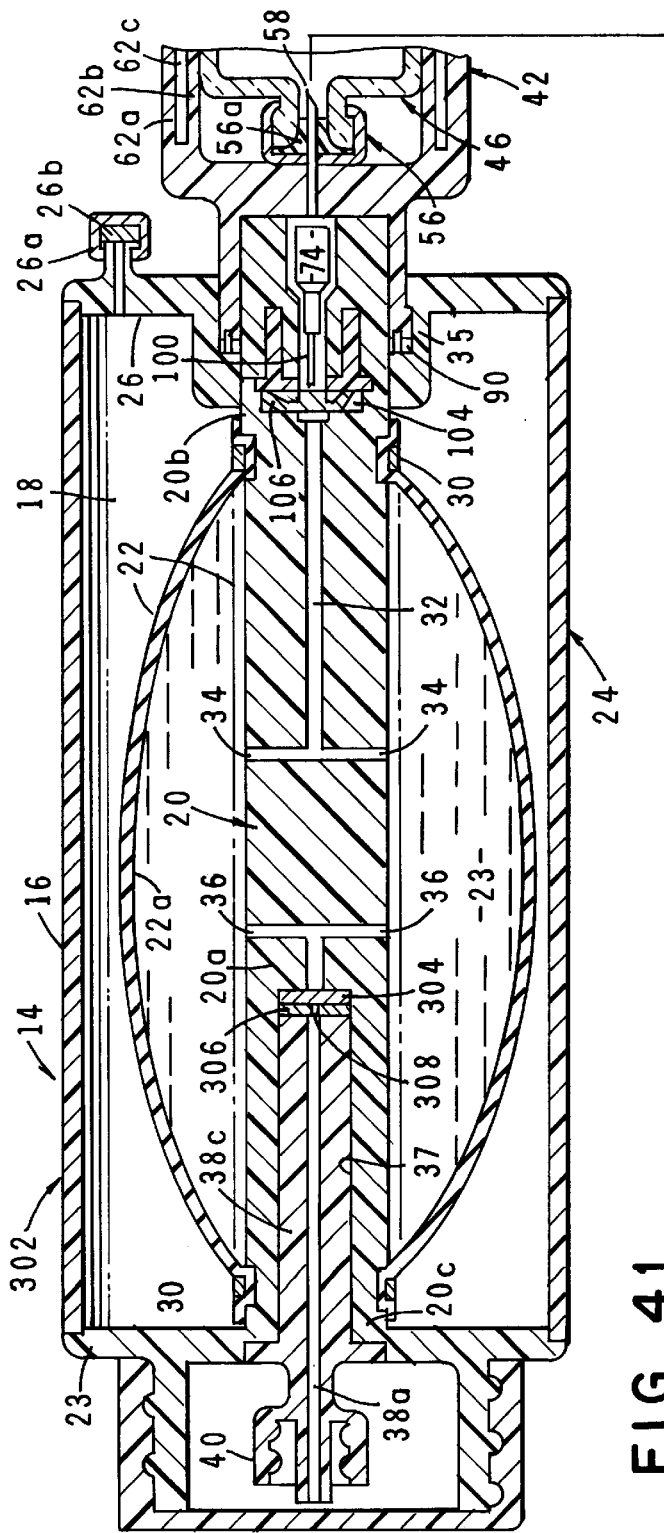
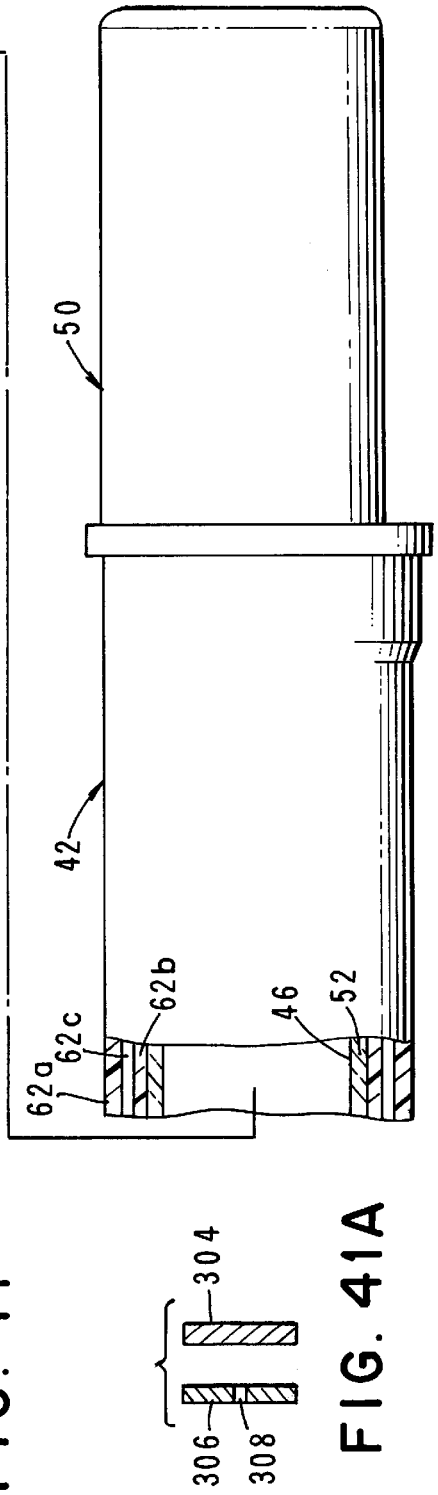
FIG. 41
FIG. 41A

FLUID DISPENSER WITH RESERVOIR FILL ASSEMBLY

BACKGROUND OF THE INVENTION

1. Field of the Invention

The present invention relates generally to infusion devices. More particularly, the invention concerns an elastomeric bladder type infusion device and cooperating reservoir fill assembly. The infusion device of the invention is used for delivering a beneficial agent to a patient at a substantially constant rate.

2. Discussion of the Prior Art

A number of infusion pumps embodying an elastomeric balloon or bladder for delivery of a quantity of pharmaceutically active material to a patient have been suggested in the past. For example U.S. Pat. No. 4,915,693 issued to Hessel discloses an infusion pump comprising an elastomeric bladder having at least an open end and an elongated stress member extending concentrically within the entire length of the hollow portion of the bladder and having a fluid tight seal therewith. Both a filling port and an exit port are provided in the stress member, each in fluid communication with the interior of the bladder by way of an influent and an effluent lumen respectively. The stress member has a diameter that is greater than the relaxed internal diameter of the bladder, and has a length that exceeds the relaxed internal length of the hollow portion of the bladder so that it prestresses the bladder in both the axial and radial directions, when disposed therein, substantially filling the bladder in its unfilled state. The Hessel device also includes a one-way valve in the stress member which permits flow in the influent lumen only in the direction of the interior of the bladder.

Another type of balloon infusion devise is disclosed in U.S. Pat. No. 4,386,929 issued to Perry et al. The Perry et al device has spaced apart inlet and outlet means and the bladder, which is capable of expanding and contracting radially and axially upon inflation and deflation. When deflated, the lumen of the bladder is substantially completely filled by lumen filling means which protect the bladder from being punctured by the hypodermic needle used to fill and inflate the bladder. The lumen filling means resists the compressive load applied during insertion of the needle and maintains the inlet and outlet means in spaced apart relationship while providing substantially no resistance to the axial expansion of the bladder. By having the lumen of the bladder filled with the lumen filling means when the bladder is deflated before its subsequent inflation and deflation, substantially complete expulsion of the fluid contents of the bladder can be obtained.

Very early balloon type devices are described in U.S. Pat. Nos. 3,468,308 and 3,469,578 issued to Bierman. These patents describe a device for expelling a liquid from a bladder member at an extremely slow rate over an extended period of time. In the device described in U.S. Pat. No. 3,469,578, the liquid is expelled slowly by pressure induced on the liquid by the internal stresses of the distended bladder member. In the device disclosed in U.S. Pat. No. 3,468,308, the liquid is expelled by pressure control means which controls pressure applied to the exterior of the bladder member to control its rate of collapse.

In the devices described in both of the aforementioned patents, the bladder member comprises a balloon, or tube-like member which is typically distendable both length wise and laterally when initially pressured. Admission and discharge of liquid is of necessity through a single neck, or outlet portion of the balloon-like bladder.

Among the more unique infusion devices ever developed are those described in U.S. Pat. Nos. 5,163,940 and 4,354,278 which were issued to the present inventor. Still another novel prior art infusion device is described in U.S. Pat. No. 5,700,244 which patent was also issued to the present inventor. Because the apparatus of the present invention constitutes an improvement over the apparatus described in the U.S. Pat. No. 5,700,244, this latter patent is hereby incorporated by reference as though fully set forth herein.

SUMMARY OF THE INVENTION

It is an object of the present invention to provide an apparatus for delivering medicaments to a patient which comprises a fluid dispensing device and a novel cooperating reservoir fill assembly. The fluid dispensing device uniquely comprises an elastomeric bladder stored energy type infusion means which can be used for delivering a wide variety of medicaments to a patient at a substantially constant rate.

More particularly, it is an object of the invention to provide an apparatus of the aforementioned character which can be used for the precise delivery to patients of selected elements, chemical compounds and biologically active materials such as drugs, medicaments, biological agents, or other therapeutic agents.

Another object of the invention is to provide a fluid dispensing device such as an elastomeric bladder type device of the class described which includes a medicament reservoir that can be conveniently filled in the field by a novel reservoir fill assembly which can be quickly and easily interconnected with the infusion device.

Another object of the present invention is to provide an apparatus of the aforementioned character in which the reservoir fill assembly includes a vial assembly of generally conventional construction that can be prefilled with a wide variety of medicinal fluids.

Another object of the present invention is to provide a reservoir fill assembly of the type described in the preceding paragraph which includes a highly novel adapter assembly that functions to conveniently removably couple the vial assembly with the fluid dispenser component of the apparatus.

Another object of the invention is to provide an adapter assembly of the type described which includes an easy-to-use bayonet type connector mechanism which conveniently mates with a dispenser connector provided on the fluid dispenser component.

Another object of the invention is to provide a novel transport and fill adapter assembly for use with the bladder type stored energy fluid dispenser subassembly of the apparatus which is easy to use, is inexpensive to manufacture, and one which maintains the prefilled vial in substantial aseptic protected condition until time of use.

Other objects of the invention will become apparent from the description which follows.

DESCRIPTION OF THE DRAWINGS

FIG. 16 is a generally perspective, fragmentary view of the forward end of the reservoir fill assembly shown in FIG. 15 illustrating the construction of the closure caps of the assembly.

FIG. 17 is an exploded view of the alternate form of the reservoir fill assembly of the apparatus of the invention shown in FIG. 15.

FIG. 18 is a cross-sectional view of yet another form of the reservoir fill assembly of the apparatus of the invention.

FIG. 19 is a cross-sectional view taken along lines 19—19 of FIG. 18.

FIG. 26 is an exploded, cross-sectional view of an alternate form of coupling mechanism for coupling together the dispenser component and the reservoir fill component.

FIG. 27 is a side-elevational view of yet another embodiment of the invention.

FIG. 31 is a generally perspective view of one of the locking tabs of the locking means of this latest form of the invention.

FIG. 32 is a cross-sectional view taken along lines 32—32 of FIG. 30.

FIG. 33 is a view taken along lines 33—33 of FIG. 30.

FIG. 34 is a view taken along lines 34—34 of FIG. 30.

FIG. 35 is a cross-sectional view taken along lines 35—35 of FIG. 30.

FIG. 36 is a view taken along lines 36—36 of FIG. 30.

FIG. 41 is a partly cross-sectional, side-elevational view similar to FIG. 1 but showing still another form of fluid flow control means.

FIG. 41A is an exploded, cross-sectional, side-elevation view of the fluid flow control means shown in FIG. 41

DESCRIPTION OF THE INVENTION

Figure 1:
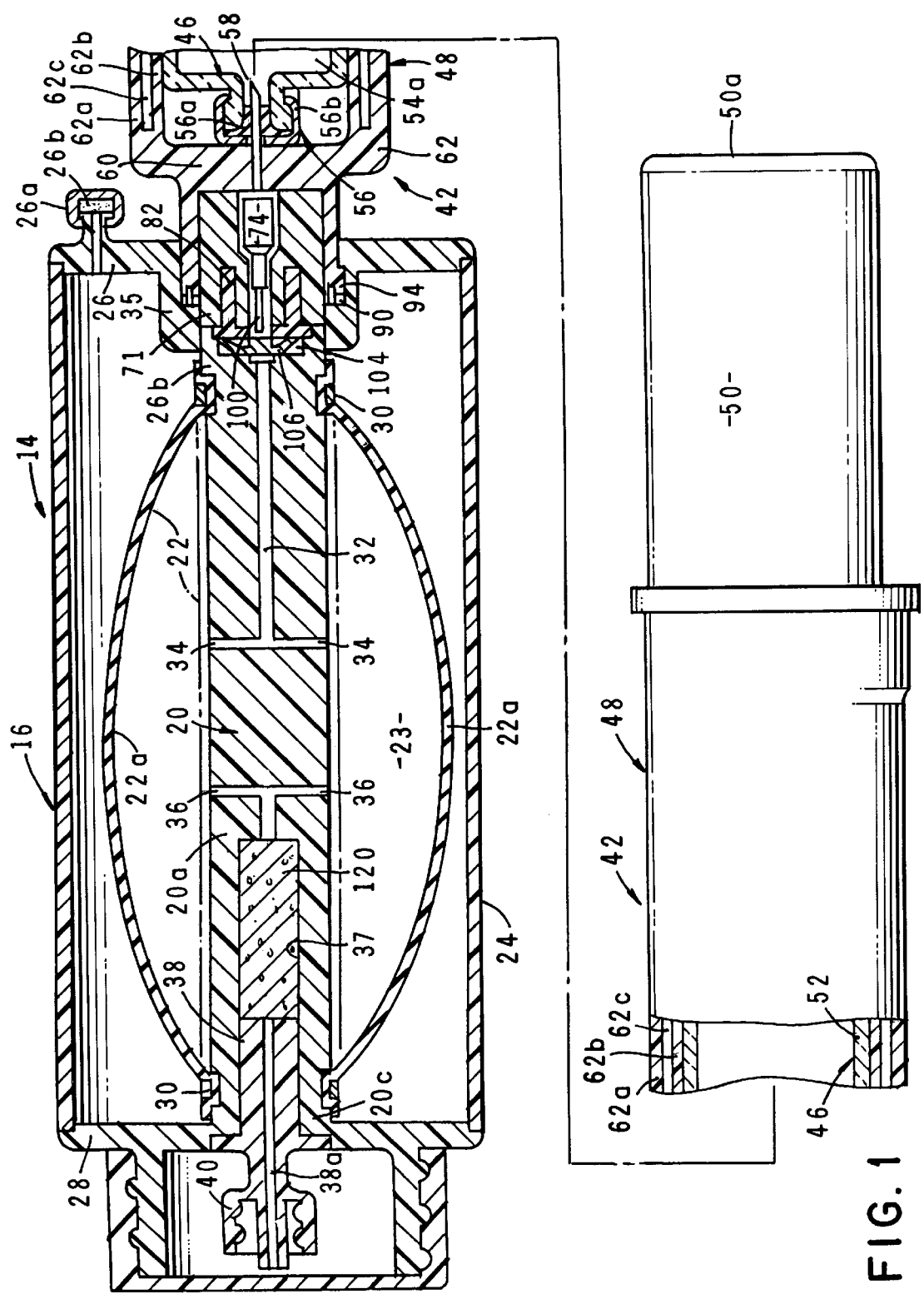
FIG. 1 is a partly cross-sectional, side-elevational view of the fluid dispensing apparatus of one form of the present invention which comprises a fluid dispenser component and a reservoir fill component.

Referring to the drawings and particularly to FIGS. 1 through 9, one form of the apparatus of the present invention is there illustrated. As best seen in FIG. 1, the apparatus here comprises two major cooperating assemblies, namely a fluid dispensing component or fluid dispenser and a reservoir fill assembly which can be operably coupled with the fluid dispenser.

As shown in FIG. 1, the fluid dispenser component, which is generally designated by the numeral 14, comprises an elongated housing 16 having an internal chamber 18, a support assembly 20 disposed within internal chamber 18, and extending longitudinally of the housing 16 and a generally cylindrically shaped, elongated elastomeric member 22. Elastomeric member 22 cooperates with support assembly 20 to define a fluid reservoir 23, the outer boundary of which is defined by the distended elastomeric member 22.

Housing 16 comprises a cylindrically shaped central portion 24 and inlet and outlet end plates 26 and 28 respectively. Central section 24 and end plates 26 and 28 can be constructed of any suitable rigid plastic material such as polycarbonate and end plates 26 and 28 can be affixed to central portion 24 by any suitable means such as adhesive bonding or an appropriate sonic weldment. Plate 26 carries a vent means for venting chamber 18 which is shown here as a vent assembly 26a which includes a filter 26b. Elastomeric stored energy member 22 is securely affixed proximate its ends to support 20a by means of suitable ring clamps 30 such as self-locking plastic panduit strips.

Figure 2:
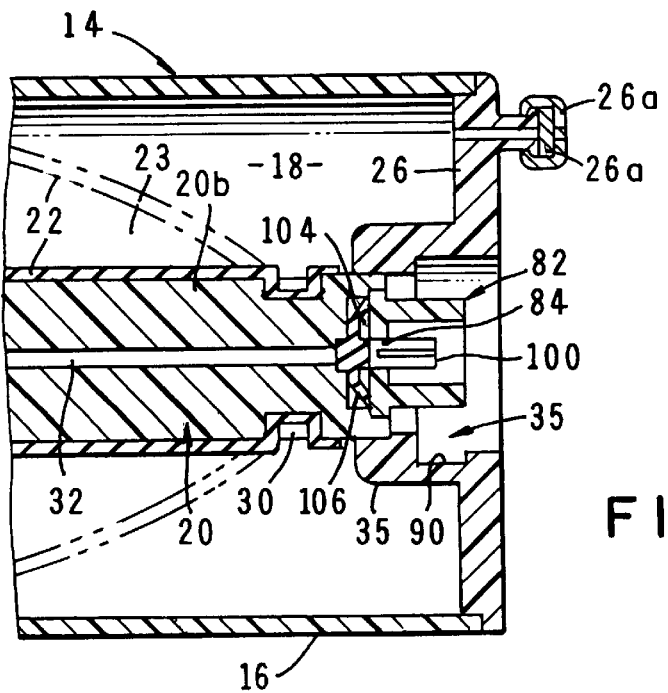
FIG. 2 is an enlarged, fragmentary, cross-sectional view of the inlet end of the fluid dispenser component of the apparatus of FIG. 1.

As shown in FIGS. 1 and 2, support assembly 20 has a first end portion 20b having a fluid inlet 32 and fluid outlets 34. Fluid inlet 32 is accessible via dispenser connector means, generally designated as 35, to which the reservoir fill component of the apparatus can be operably connected.

Support assembly 20 also includes a second end portion 20c (FIG. 1) having inlet fluid passageway 36 and an elongated internal chamber 37. Received within chamber 37 is a flow control means, the character of which will presently be discussed. Also received within the outboard end of chamber 37 is a connector insert 38 having an outlet fluid passageway 38a. A fluid dispensing means shown here as comprising a luer connector 40 is provided proximate the outboard end of connector insert 38 in the manner shown in the drawings. It is to be observed that elastomeric member 22 includes a central portion generally designated as 22a which, in its starting position as shown by the phantom lines in FIG. 1, overlays fluid outlet passageways 34 and fluid inlet passageways 36 of support assembly 20.

The dispensing device 14 of the present invention is similar in many respects to that described in U.S. Pat. No. 5,700,244 which is incorporated herein by reference This latter patent should be referred to for a more detailed description of the details of construction of and materials suitable for use in forming the various components of the fluid dispenser component of the invention including elastomeric stored energy member 22.

Figure 3:
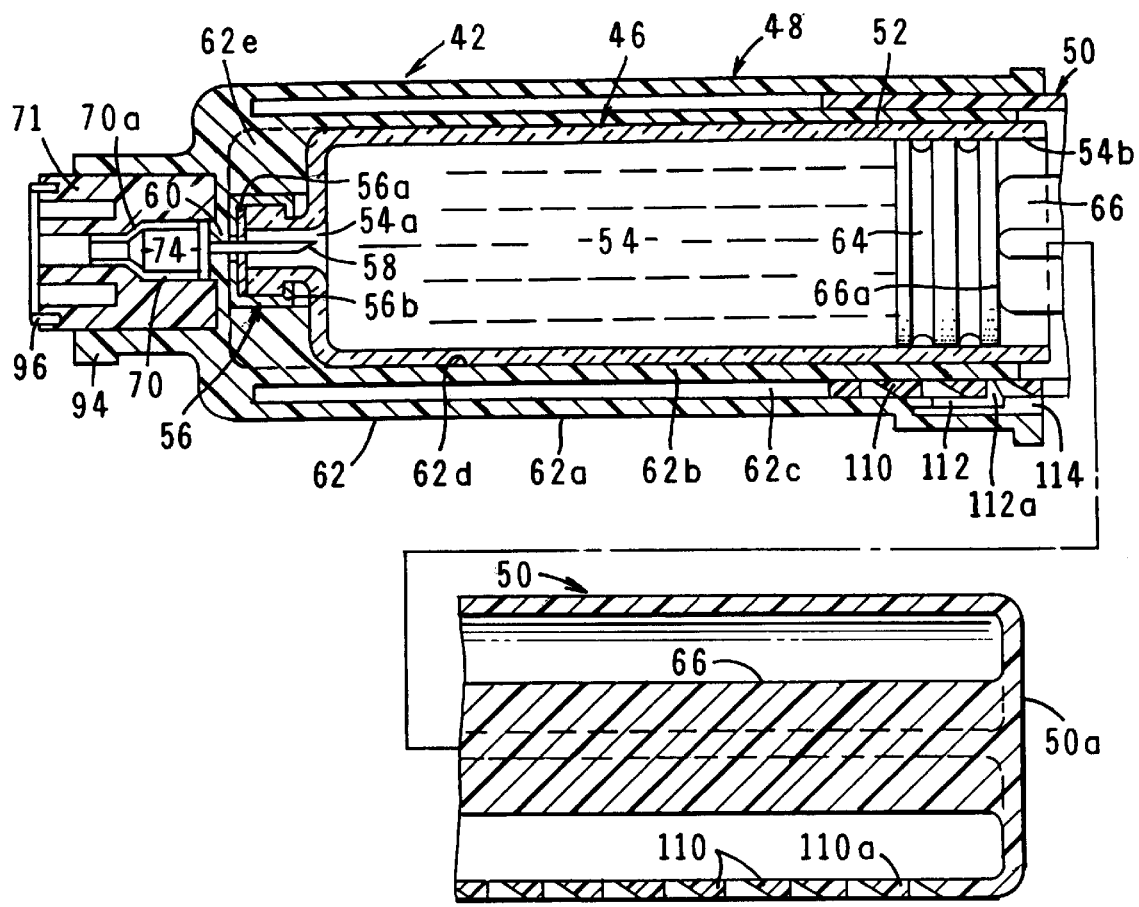
FIG. 3 is an enlarged, fragmentary, cross-sectional exploded view of the reservoir fill component of the apparatus of FIG. 1.
Figure 12:
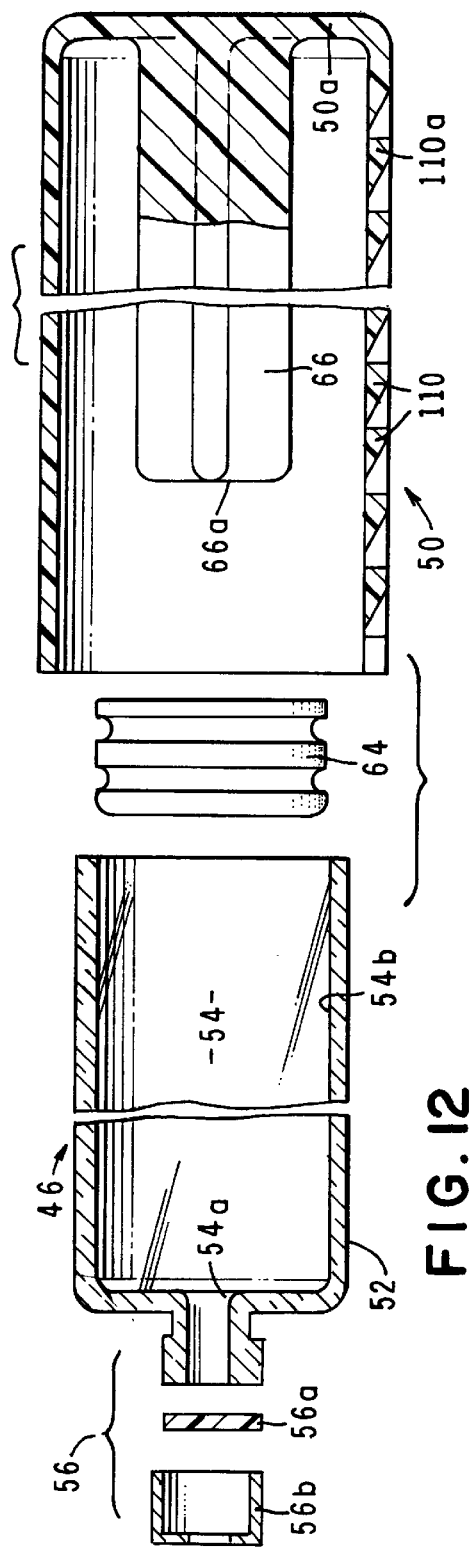
FIG. 12 is an enlarged, cross-sectional, exploded view of the container and pusher sleeve subassemblies of the apparatus of the invention.

Turning particularly to FIGS. 3 through 12, the novel reservoir fill assembly of the invention, which is generally designated by the numeral 42, can be seen to comprise three major components, namely a container subassembly 46 (FIG. 12), an adapter subassembly 48 (FIG. 5) and an adapter or pusher sleeve 50 (FIGS. 3 and 12). Container subassembly 46 includes a container such as a vial 52 which contains the medicinal fluid "F" with which the reservoir 23 of the dispensing apparatus is to be filled. Adapter subassembly 48 functions to interconnect the reservoir fill assembly 42 with the dispenser component 14 in the manner presently to be described so that fluid can be transferred from container 52 to the reservoir 23 of the dispenser component.

Figure 5:
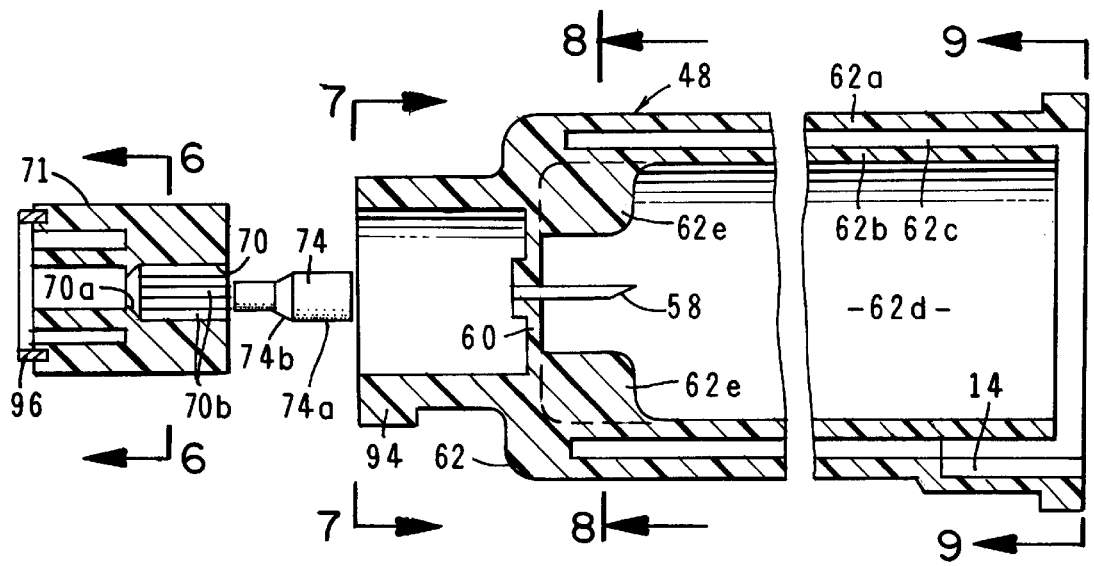
FIG. 5 is an enlarged, cross-sectional, exploded view of the adapter subassembly of the reservoir fill assembly.

As best seen in FIGS. 3 and 12, container subassembly 46 includes a fluid chamber 54 having first and second open ends 54a and 54b. First open end 54a is sealably closed by closure means, here provided in the form of septum assembly 56 which includes a pierceable septum 56a and a clamping ring 56b for connecting the septum to the container proximate open end 54a. Septum 56a is pierceable by the cannula means or cannula 58 of the adapter subassembly 48 which forms a part of the fill flow control means of the invention. As shown in FIG. 5, cannula 58 is mounted centrally of an end wall 60 of body 62 of the adapter subassembly.

To expel fluid from fluid chamber 54 of the vial assembly and into hollow cannula 58 of the adapter subassembly and thence into the fluid reservoir 23 of the dispenser unit, a plunger 64 is telescopically movable within chamber 54 by pusher sleeve 50. To accomplish this movement, sleeve 50 is provided with pusher means shown here as a pusher rod 66 which is integrally formed with end wall 50a of sleeve 50 (see FIG. 12).

Referring once again particularly to FIGS. 3 and 5, it is to be noted that body 62 of fill adapter subassembly 48 includes outer and inner, generally cylindrically shaped walls 62a and 62b which define therebetween an elongated annular space 62c and within which the inboard end of sleeve component 50 is telescopically received. As shown in FIG. 3, container assembly 46 is closely receivable with a chamber 62d formed internally of wall 62b of the adapter subassembly and can be urged forwardly of chamber 62d by inward telescopic movement of sleeve 50 into space 62c. More particularly, the inboard end 66a of pusher rod 66 engages plunger 64 and urges it inwardly of reservoir 54 as sleeve 50 is moved inwardly of annular space 62c.

Figure 6:
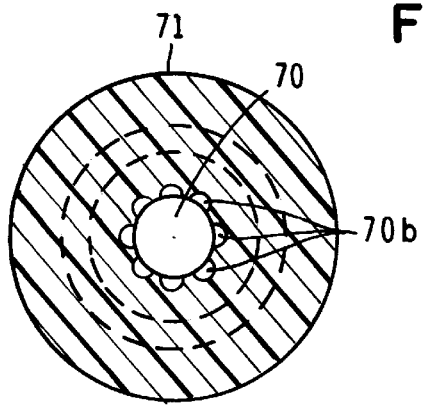
FIG. 6 is a cross-sectional view taken along lines 6—6 of FIG. 5.
Figure 7:
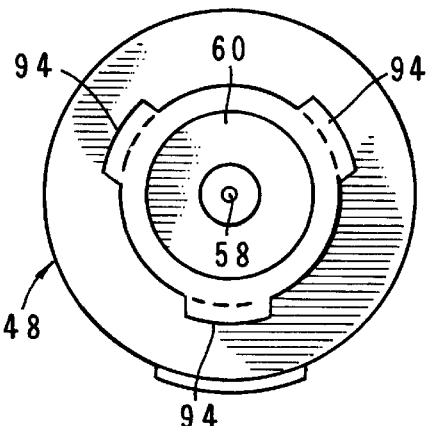
FIG. 7 is a view taken along lines 7—7 of FIG. 5.
Figure 8:
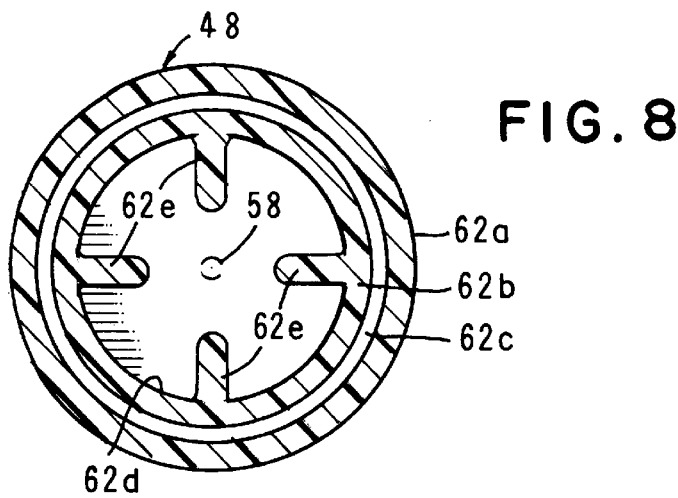
FIG. 8 is a cross-sectional view taken along lines 8—8 of FIG. 5.
Figure 9:
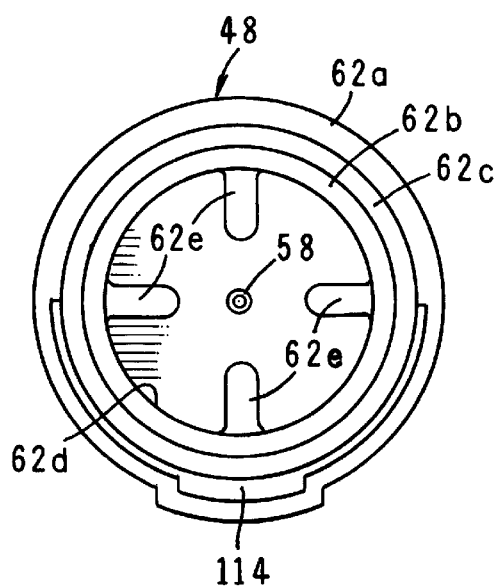
FIG. 9 is a view taken along lines 9—9 of FIG. 5.
Figure 10:
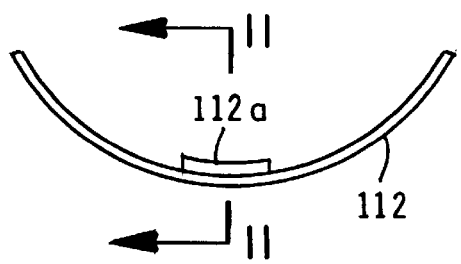
FIG. 10 is an end view of the locking tab portion of the locking means of the invention for locking the pusher sleeve subassembly of the reservoir fill assembly to the adapter component thereof.
Figure 11:
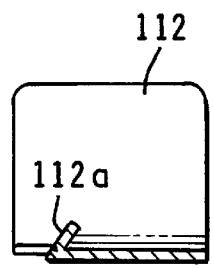
FIG. 11 is a cross-sectional view taken along lines 11—11 of FIG. 10.

During the initial mating of sleeve 50 with adapter subassembly 48, the resistance of the fluid within chamber 54 will resist movement of plunger 64 inwardly of reservoir 54 so as to cause the entire vial cartridge assembly to initially move inwardly of chamber 62d to a position wherein septum 56a is engaged by cannula 58 of the adapter subassembly. As shown in FIGS. 5 and 8, guide ribs 62e formed interiorly of chamber 62d, guide the neck portion of the vial toward cannula 58. A continued inward force on sleeve 50 will cause cannula 58 to pierce septum 56a in the manner shown in FIGS. 1 and 3, thereby opening fluid communication between reservoir 54 of vial 46 and the internal fluid passageway of cannula 58. Once septum 56a has been penetrated, pusher rod 66 will urge plunger 64 forwardly of reservoir 54 from a first location proximate open end 54b to a second location proximate end 54a. As plunger 64 moves forwardly of reservoir 54, fluid within the reservoir will be caused to flow into the central fluid passageway of cannula 58 and toward another portion of the fill flow control means of the invention which controls fluid flow toward the fluid dispenser component 14. This flow control means includes valve means which comprises a valve chamber generally designated in FIG. 5 by the numeral 70. Valve chamber 70, which is formed in the connector portion 71 of reservoir fill assembly 42 includes a valve seat 70a. As best seen in FIG. 6, valve chamber 70 is provided with a plurality of circumferentially spaced fluid flow grooves 70b. Disposed within chamber 70 is a check valve 74, which also comprises a part of the valve means for permitting fluid flow from hollow cannula 58 toward the fluid reservoir of the dispenser assembly. As shown in FIG. 5, check valve 74, which is of conventional construction, includes a body portion 74a and a seat portion 74b which sealably engages seat 70a when valve 74 is in a closed position. The construction and operation of the valve means is well understood by those skilled in the art and the manner of opening the valve during the filling step will presently be described.

Figure 14:
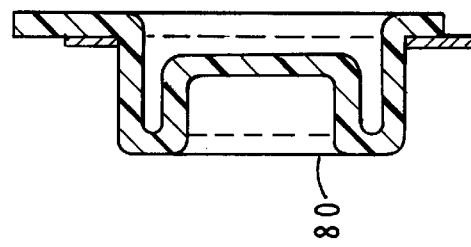
FIG. 14 is an enlarged, cross-sectional view of the closure cap for sealing the inlet port of the dispenser component.
Figure 13:
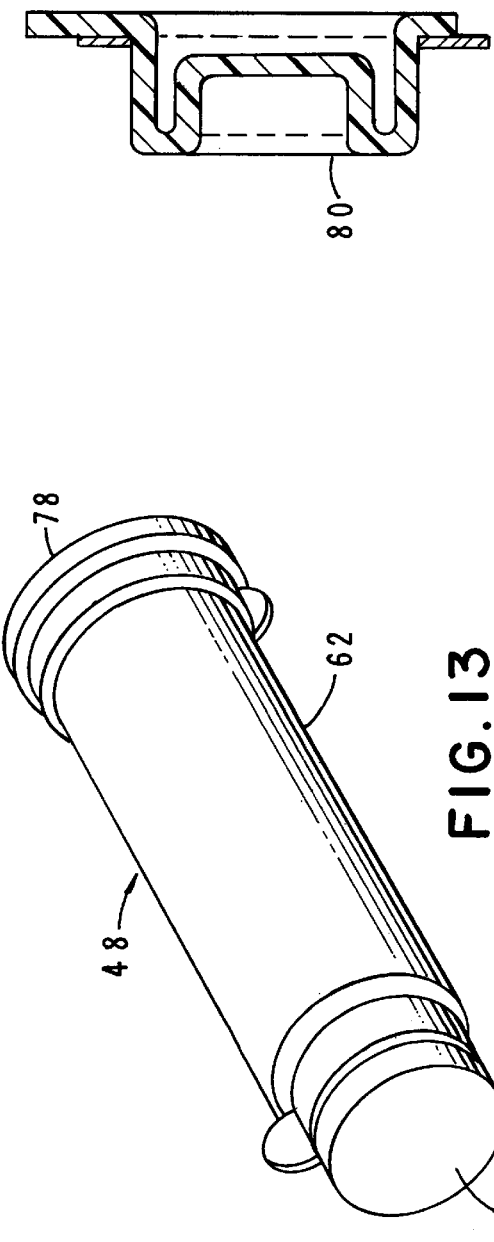
FIG. 13 is a generally perspective view of the adapter subassembly of the invention prior to use.

Prior to use, adapter subassembly 48 is maintained in a protected and substantially sterile configuration by tear-away end caps 76 and 78 (see FIG. 13). As indicated in FIG. 13, tear-away end cap 76 is receivable over and closes the forward end of adapter subassembly 48, while tear-away end cap 78 is received over and closes the rearward open end portion of adapter subassembly 48. Similarly, a barrier tear-away cap 80 of the configuration shown in FIG. 14 can be emplaced over the dispenser connector means which here comprises a dispenser connector subassembly 82 having inlet portion 84 (FIG. 2). When in place, cap 80 maintains the dispenser connector assembly and fluid inlet passageway of the device in a closed and substantially sterile condition.

At the time of use of the apparatus of the invention, and with the adapter assembly 48 in the sealed condition shown in FIG. 13, closure cap 76 is first removed from the assembly. This done, the assembly can be mated with the connector means of the dispenser component 14 in the manner shown in FIG. 1 and lockably interconnected therewith by the fill connector means which here comprises a bayonet type connector arrangement of the character best seen in FIGS. 5, and 7. More particularly, as shown in FIGS. 1 and 2, the dispenser connector means includes a plurality of circumferentially spaced-apart tab receiving slots 90. Similarly, the inboard end of the adapter subassembly 48 is provided with an adapter connector comprising a plurality of circumferentially spaced apart locking ears 94 (FIGS. 5 and 7) which are adapted to be received within slots 90. With this construction, after locking ears 94 have been received within slots 90, rotation of adapter subassembly 48 relative to the dispensing means will bring ears 94 into locking engagement with the dispenser unit thereof operably interconnecting the reservoir fill assembly 42 with the dispenser unit 14. To enable smooth rotation of the adapter subassembly relative to the dispenser unit, an antilock elastomeric ring 96 is formed on the front face of member 71 (FIG. 5).

During the mating of the adapter assembly 48 with the dispenser unit 14, an extension 100 provided on connector subassembly 82 (FIG. 2) functions as a valve operating means to move valve 74 of the valve means away from seat 70a. During mating, elastomeric ring 96 sealably mates with connector means 35 to form a substantially leak-tight seal.

With adapter subassembly 48 suitably mated with the dispenser 14, cap 78 is removed from the outboard end of adapter assembly 48 (FIG. 13) and the first end of the vial assembly 46 is inserted into chamber 62d of adapter subassembly 48. With the vial cartridge assembly inserted into chamber 62d, sleeve 50 is then mated with adapter assembly 48 in the manner shown in FIG. 1 by inserting the leading edge of the pusher sleeve into annular space 62c. A forward movement of the pusher sleeve into annular space 62c will cause pusher rod 66 to move into pressural engagement with plunger 64 causing the entire vial assembly to move forwardly within chamber 62d to the position where cannula 58 of the adapter subassembly interengages pierceable septum 56a of the container assembly. A continued inward force on the pusher sleeve 50 will cause hollow cannula 58 to pierce septum 56a thereby opening fluid communication between chamber 54 of vial 52 and valve chamber 70. Exertion of a continued inward pressure on pusher sleeve 50 will cause plunger 64 to move forwardly of vial chamber 54 causing the fluid contained within reservoir 54 to flow into hollow cannula 58 and past check valve 74. Because valve member 74 of the adapter assembly has been moved away from seat 70a by extension 100, fluid will flow into bypass flow channels 70b formed in chamber 70. The fluid under pressure will next flow into a chamber 104 formed in end portion 20b of support 20. Disposed within chamber 104 is an umbrella valve 106 which also forms a part of the dispenser flow control means of the invention and is of a construction well known to those skilled in the art. Umbrella valve 106 permits fluid flow toward passageway 32 but blocks flow in the opposite direction. As the fluid under pressure flows through inlet passageway 32 and 34, the stored energy means or elastomeric member 22 will be distended in the manner shown in FIG. 1 causing internal stresses to be built up within the elastomeric member, which stresses tend to return the member toward its less stressed starting configuration. With reservoir 23 thusly filled, valve member 106 will prevent fluid flow in a direction toward the reservoir fill assembly 42.

Figure 4:
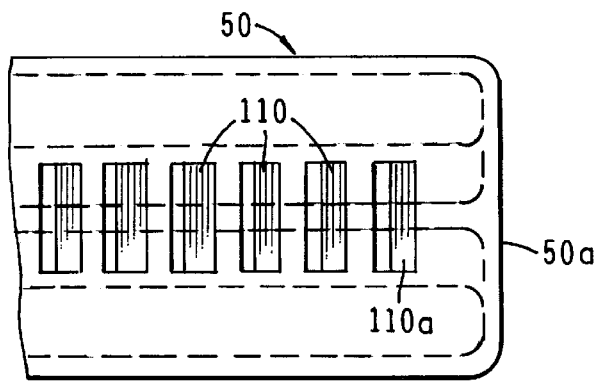
FIG. 4 is a fragmentary top plan view of a portion of the adapter sleeve of the reservoir fill assembly showing the locking teeth formed thereon.

Turning particularly to FIG. 4, it is to be noted that pusher sleeve 50 is provided with a plurality of longitudinally spaced, upstanding teeth 110 which form a part of the locking means of the invention for locking sleeve 50 to the adapter subassembly after filling of reservoir 23. As sleeve 50 is inserted into annular space 62c, teeth 110 will slide under an inwardly extending tab 112a provided on a locking clip 112 (FIGS. 3, 10, and 11) which also form a part of the locking means and which is carried within a relief 114 formed in adapter assembly 48 in the manner shown in FIGS. 3 and 9. When sleeve 50 is fully inserted into annular space 62c, tab 112a will lockably engage rearward most tooth 110a preventing withdrawal of the sleeve from space 62c.

At any time after the reservoir filling step, the adapter assembly 48, or transporter fill assembly can be disconnected from the dispenser unit by counter-rotation thereof and the fluids contained within reservoir 23 can be delivered to the patient by affixing an infusion line to luer connector 40. Opening of the infusion line will permit the stored energy means or member 22 to move toward its first less distended configuration shown in FIG. 2 thereby controllably urging fluid flow outwardly of the device via the dispenser flow control. The dispenser flow control means comprises, in addition to umbrella valve 106, a porous plug 120 which is disposed within chamber 37 in the manner best seen in FIG. 1. Plug 120 can be constructed from various sintered metal, plastic and ceramic materials. However, a porous polycarbonate material available from Poretics Corporation or from Corning Costar Corporation has proven satisfactory.

As shown in FIG. 41, plug 120 can be replaced by the flow control means there shown which comprises a filter means or filter 304 and a laser-machined, single-hole orifice provided in flow control element 306.

Figure 15:
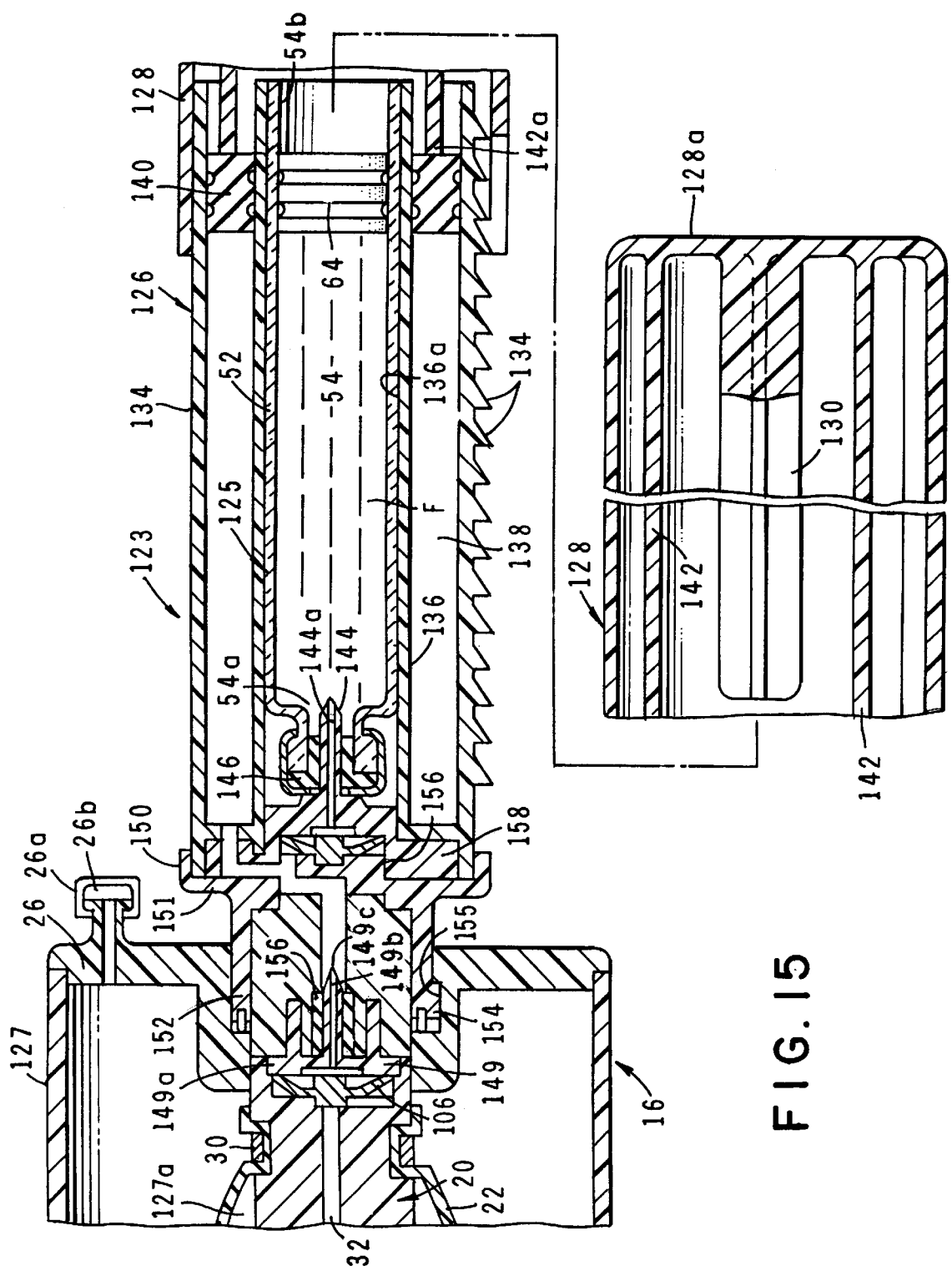
FIG. 15 is a cross-sectional view of another form of the fluid dispenser of the invention showing the dispenser component operably mated with an alternate form of reservoir fill assembly.

Turning next to FIG. 15, another embodiment of the present invention is there shown. In this latest embodiment, the fluid dispenser component is quite similar to that previously described as is the fill assembly. Accordingly, where appropriate, like numbers are used to designate like components. Once again, this latest embodiment of the reservoir fill assembly, which is generally designated by the numeral 123 comprises three major components, namely a container subassembly 125 which is substantially identical to that previously described, an adapter subassembly 126 which is of slightly different construction from that previously described, and an adapter or pusher sleeve 128 which is also somewhat similar to that previously described. As before, container or vial subassembly 125 includes a container such as a vial 52 which contains the medicinal fluid "F" with which the reservoir of the dispensing apparatus is to be filled. As in the earlier described embodiments, the adapter subassembly 126 functions to provide a sterile interconnection which interconnects the reservoir fill assembly with the fluid dispenser component 127 by a similar bayonet locking system and in a manner such that fluid can be transferred from container 52 to the reservoir 127a of the fluid dispenser component. This fluid transfer is accomplished by urging sleeve 128 forwardly over the adapter subassembly in the manner previously described. More particularly, to expel fluid from fluid chamber 54 of container 52 and into reservoir 127a of the dispenser component, a plunger 64 is telescopically movable within chamber 54 by pusher sleeve subassembly 128 which includes pusher means shown here as a pusher rod 130 which, as before, is integrally formed with end wall 128a of the sleeve.

It is to be observed that, as before, adapter subassembly 126 of this last embodiment of the invention includes an outer, generally cylindrically shaped wall 134 and an inner, generally cylindrically shaped wall 136 which define therebetween an elongated annular space 138 within which a generally ring shaped elastomeric ring 140 is moved longitudinally by an end wall 142a of an inner, generally cylindrically shaped wall 142 which forms a part of pusher sleeve 128 and which extends inwardly from the end wall 128a thereof. Annular space 138 comprises a diluent reservoir for containing a suitable diluent. Container assembly 125 is closely receivable within a chamber 136a formed internally of wall 136 of the adapter subassembly and can be urged forwardly of chamber 136a by inward movement of sleeve 128 relative to adapter assembly 126 in a manner such that the outer wall of pusher sleeve 128 slides over outer wall 134 of the adapter subassembly and end 142a inner wall 142 engages ring 140. As the pusher sleeve moves forwardly, it will urge ring 140 forwardly of space 138 causing the diluent to be expelled therefrom.

Following interconnection of the reservoir fill assembly with the dispenser unit in the manner previously described and as shown in FIG. 15, a continued exertion of an inward force on sleeve 128 will cause a blunt end cannula 144 of the adapter subassembly 126 to pierce a slit septum 146 of container subassembly 125 in the manner shown in FIG. 15. Blunt end cannula 144 forms a part of the fill flow control means of the invention for controlling fluid flow toward the dispenser component. This action opens fluid communication between reservoir 54 of vial 52 and the internal fluid passageway 144a of blunt end cannula 144 which is of a character well known to those skilled in the art. Once slit septum 146 has been pierced, pusher rod 130 will urge plunger 64 forwardly of reservoir 54 from a first location proximate open end 54b to a second location proximate end 54a. As plunger 64 moves forwardly of reservoir 54, fluid within the reservoir will be caused to flow into cannula passageway 144a for delivery toward the reservoir 127a of the fluid dispenser via a hollow blunt end cannula assembly 149 which forms a part of the dispenser flow control means of the invention for controlling fluid flow outwardly of the apparatus toward the patient (FIG. 15). During this reservoir filling step, the diluent contained within annular space 138 will, due to the urging of ring 140, be caused to flow toward cannula assembly 149 via a passageway 127a formed in wall 129 of adapter 123. As the medicament from vial 52 and the diluent from space 138 flow toward cannula assembly 149, the fluids will be intermixed to form the fluid to be infused into the patient. Details of construction of this latest form of fluid dispenser will presently be described.

As shown in FIG. 15, a cover member 150 is connected to wall 134 of the adapter body by any suitable means such as sonic bonding. Cover 150 includes a flanged plate portion 151 and a generally cylindrically shaped extension 152 integrally formed with plate 151. Formed proximate the outboard end of extension 152 are connector means shown here as circumferentially spaced locking tabs 154 which mate with locking slots provided in the dispenser component. Plate 151 of cover 150 includes a generally circular shaped internal recess 156 which receives a cannula support plate 158 which plate supports cannula 144 in the manner shown in FIG. 15.

Prior to use, the adapter assembly can be sealed by tear-away caps 76 and 78 (FIG. 13) of the general character previously described. Following removal of cap 76, the reservoir fill assembly can be lockably mated with the fluid dispenser in the manner previously described by inserting tabs 154 of the bayonet type locking means into mating openings 155 provided in the inlet end plate 26 of the fluid dispenser and rotating the fill assembly relative to the dispenser.

It is to be observed that, as previously mentioned, the fluid dispenser of this latest form of the delivery apparatus is quite similar to that shown in FIGS. 1 and 2. However in the fluid dispenser construction shown in FIG. 15, the valve operating extension 100 has been replaced with hollow cannula assembly 149 which includes a cannula support plate 149a and a hollow cannula 149b having a fluid passageway 149c. Similarly, valve member 74 has been replaced by a slit septum 156 which is readily pierceable by cannula 149b.

Turning next to FIGS. 16 through 25, still another embodiment of the present invention is there shown. In this latest embodiment, the fluid dispenser component is substantially identical to that shown in FIG. 15. Additionally, the reservoir fill assembly is quite similar to that previously described other than the fact that certain parts thereof are differently configured. Accordingly, where appropriate, like members are again used to designate like components. This latest embodiment of the reservoir fill assembly, which is generally designated by the numeral 160 also comprises three major components, namely a container subassembly 125 which is substantially identical to that previously described, an adapter subassembly 164 which is of slightly different construction from that previously described, and an adapter or pusher sleeve 166 which is also somewhat similar to that previously described but has a slightly different shape.

As before, container or vial subassembly 125 includes a container such as a vial 52 which contains the medicinal fluid "F" with which the reservoir of the dispensing apparatus is to be filled. As in the earlier described embodiments, the adapter subassembly 164 functions to interconnect the reservoir fill assembly with the fluid dispenser component 127 in a manner previously described so that fluid can be transferred from container 52 to the reservoir 127a of the fluid dispenser (FIG. 15). This fluid transfer is once again accomplished by urging sleeve 166 forwardly over the adapter subassembly in the manner indicated in FIG. 18. More particularly, to expel fluid from fluid chamber 54 of container 52 and into reservoir 127a of the dispenser component, a plunger 64 is telescopically movable within chamber 54 by pusher sleeve subassembly 166 which includes pusher means shown here as a pusher rod 166a which, as before, is integrally formed with end wall 166b of the sleeve.

Referring particularly to FIGS. 16, 17, 19, and 20 it is to be noted that adapter subassembly 164 of this last embodiment of the invention includes an outer, generally elliptical shaped wall 170 and an inner, generally cylindrically shaped wall 172 which define therebetween an elongated, annular-like reservoir 174 within which an elliptically shaped sealing ring 176 is moved longitudinally by the end wall 177a of an inner wall 177 formed as a part of pusher sleeve 166. Once again, reservoir 174 contains a diluent which is intermixed with the medicinal agent contained within vial 52 during the filling of the dispenser reservoir. Container assembly 125 is closely receivable within a chamber 172a formed internally of wall 172 of the adapter subassembly and can be urged forwardly of chamber 172a by inward movement of sleeve 166 relative to adapter assembly 164.

Following interconnection of the reservoir fill assembly with the dispenser unit, in the manner previously described, a continued exertion of an inward force on sleeve 166 will cause a cannula 180 of the adapter subassembly 164 to pierce a septum 146 of the container subassembly in the manner shown in FIG. 18. This action opens fluid communication between reservoir 54 of vial 52 and the internal fluid passageway 180a of cannula 180. Once septum 146 has been pierced, pusher rod 166a will urge plunger 64 forwardly of reservoir 54 from a first location proximate open end 54b to a second location proximate end 54a. As plunger 64 moves forwardly of reservoir 54, fluid within the reservoir will be caused to flow into cannula passageway 180a for delivery toward the reservoir of the fluid dispenser via a hollow cannula assembly 149 of the character shown in FIG. 15. As sleeve 166 moves forwardly, ring 176 will be urged forwardly of space 174 causing the diluent contained within the space to be urged to flow through passageway 165a of adapter 164.

Figure 20:
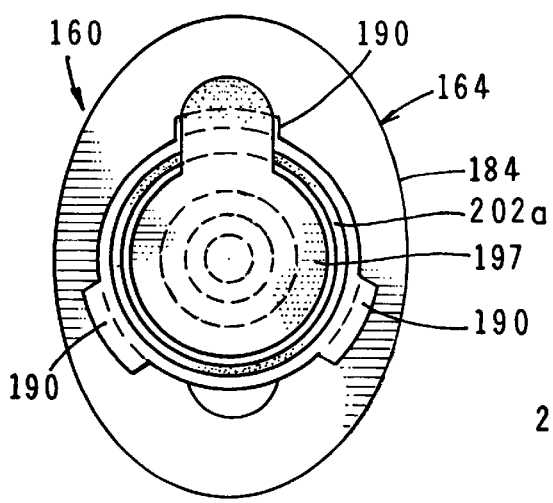
FIG. 20 is a view taken along lines 20—20 of FIG. 18.
Figure 21:
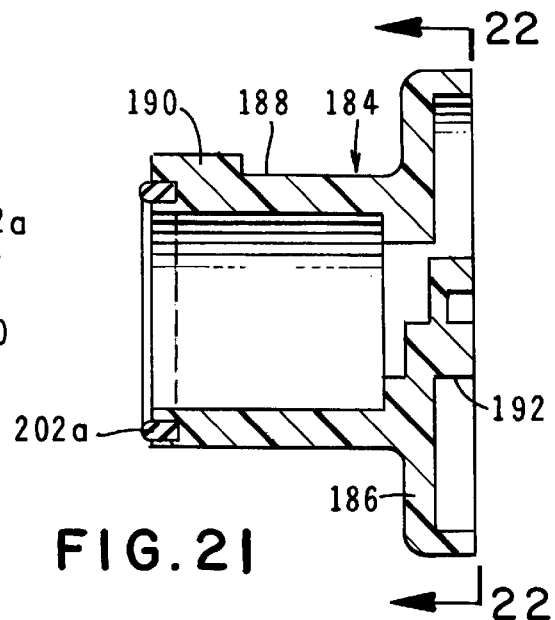
FIG. 21 is a cross-sectional view of the reservoir fill assembly housing cover of the assembly shown in FIG. 18.
Figure 22:
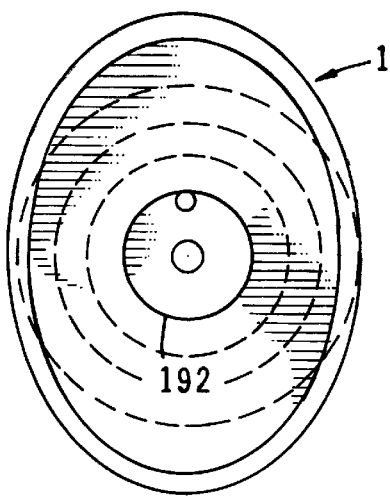
FIG. 22 is a view taken along lines 22—22 of FIG. 21.
Figure 24:
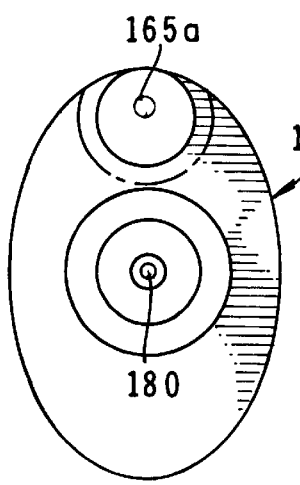
FIG. 24 is a view taken along lines 24—24 of FIG. 23.
Figure 23:
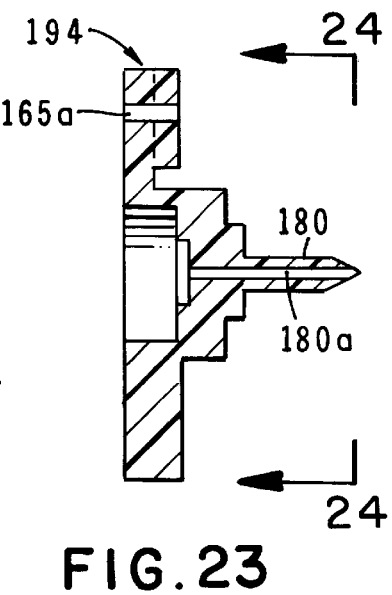
FIG. 23 is a cross-sectional view of the cannula subassembly of the reservoir fill assembly shown in FIG. 18.

As best seen in FIGS. 18, 20, and 21, a cover member 184 is connected to wall 170 of the adapter body by any suitable means such as sonic bonding. Cover 184 includes a flanged plate portion 186 and a generally cylindrically shaped extension 188 which is integrally formed with plate 186 (FIG. 21). Formed proximate the outboard end of extension 188 are connector means shown here as circumferentially spaced locking tabs 190. Plate 186 of cover 184 includes a generally circular shaped internal recess 192 which receives a cannula support plate 194 which plate supports blunt end cannula 180 (FIGS. 18 and 23).

Figure 25:
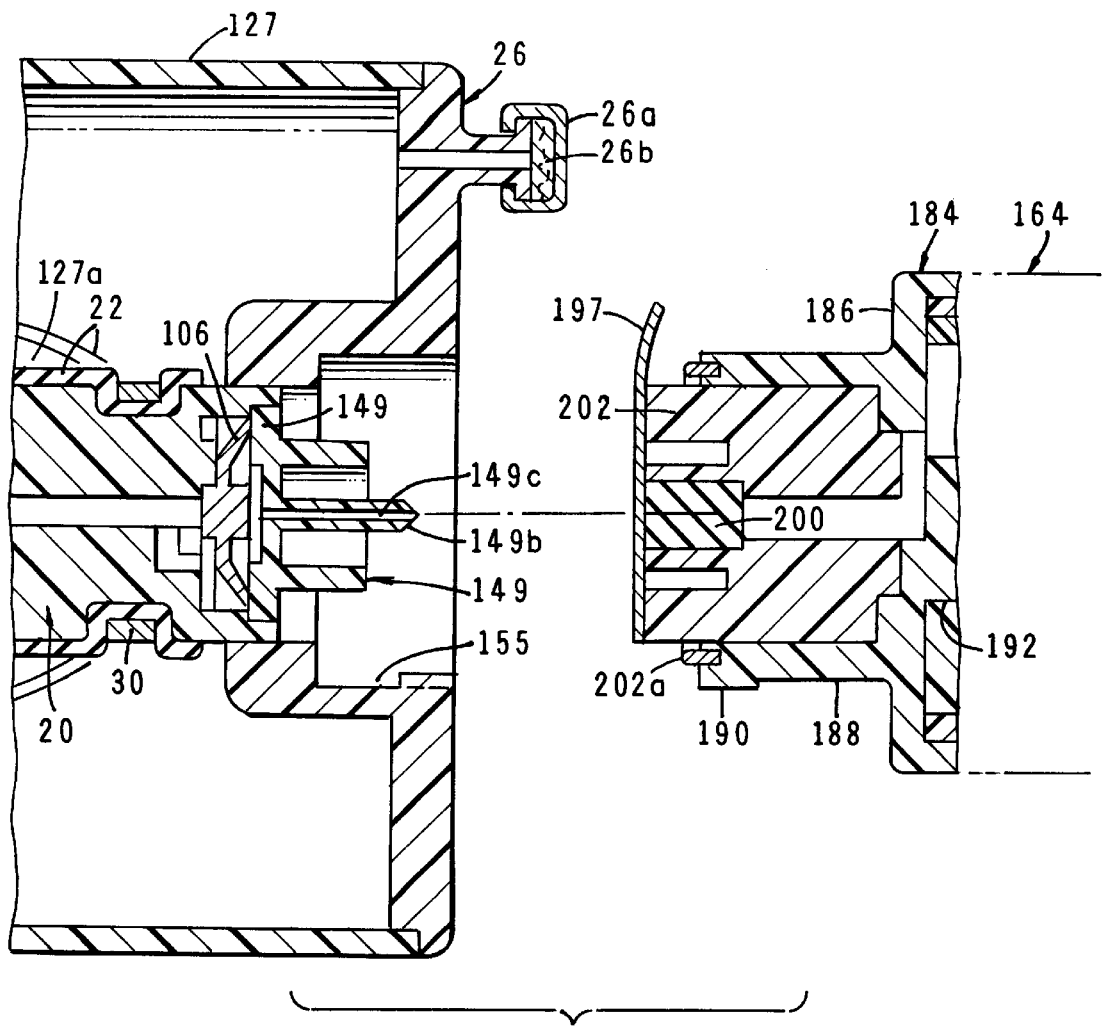
FIG. 25 is an enlarged, cross-sectional, exploded view of the coupler mechanism of this latest form of the invention.

Prior to use, the adapter assembly is sealed by a peel-away seal 197 and a tear-away cap 199 (FIGS. 16 and 25). Following removal of seal 197 and cap 199, the reservoir fill assembly can be lockably mated with the fluid dispenser in the manner previously described by inserting tabs 190 into the openings 155 provided in the inlet end plate 26 of the fluid dispenser (FIG. 25).

As shown in FIG. 25, the fluid dispenser of this latest form of the delivery apparatus includes the previously discussed hollow cannula assembly 149 which is designed to pierce a slit septum 200 which is carried within a septum support member 202 that is mounted within extension 188 of cover member 184 in the manner shown in FIG. 25. Extension 188 of cover member 184 is provided with an elastomeric ring 202*a* which prevents seizing during the mating step and which provides a seal between the mated components.

It is to be understood that the same type of coupling mechanism depicted in FIGS. 1 through 7 can be used in the dispenser embodiment shown in FIG. 25. For example, the same type of dispenser connector 82 with extension 84 could be used in lieu of cannula assembly 149 and a valve member such as a valve member 74 shown in FIGS. 1 and 3 could be used in lieu of septum 200.

Additionally, as shown in FIG. 26 where like numbers are used to identify like components, the dispenser connector could comprise a slit septum 204 and the fill reservoir connector could be provided with a cannula assembly 206 which comprises a cannula support 206*a* and a blunt end hollow cannula 206*b*. A barrier-type peel-away cover 197 is used to protect cannula 206*b*.

Referring next to FIGS. 27 through 38, yet another alternate embodiment of the apparatus of the invention is there shown. As before, the apparatus comprises a fluid dispenser and a cooperating reservoir fill assembly (FIG. 27). The dispenser component 14 is identical in construction and operation to that shown in FIGS. 1, 2, and 3 and like numerals are used to identify like components.

Figure 28:
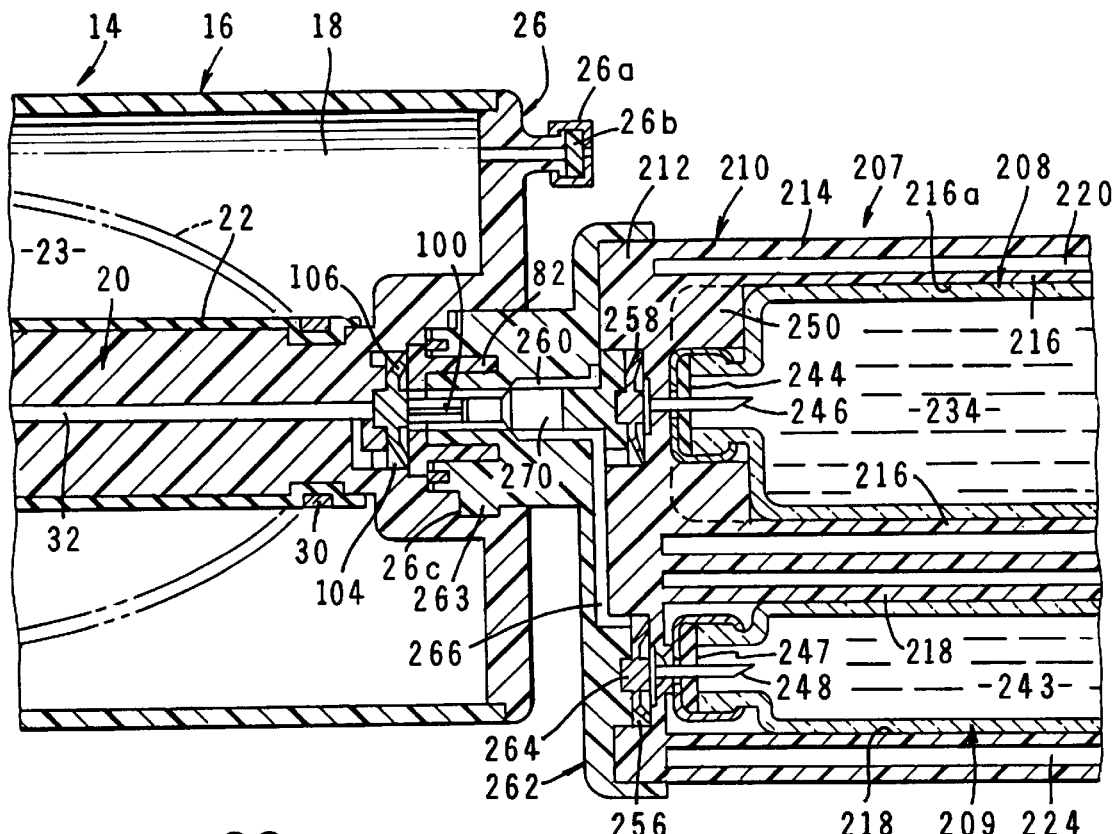
FIGS. 28 and 28A comprise, when taken together, an enlarged, cross-sectional view of the alternate form of the apparatus of the invention shown in FIG. 27 which includes a dual vial reservoir fill assembly.
Figure 28A:
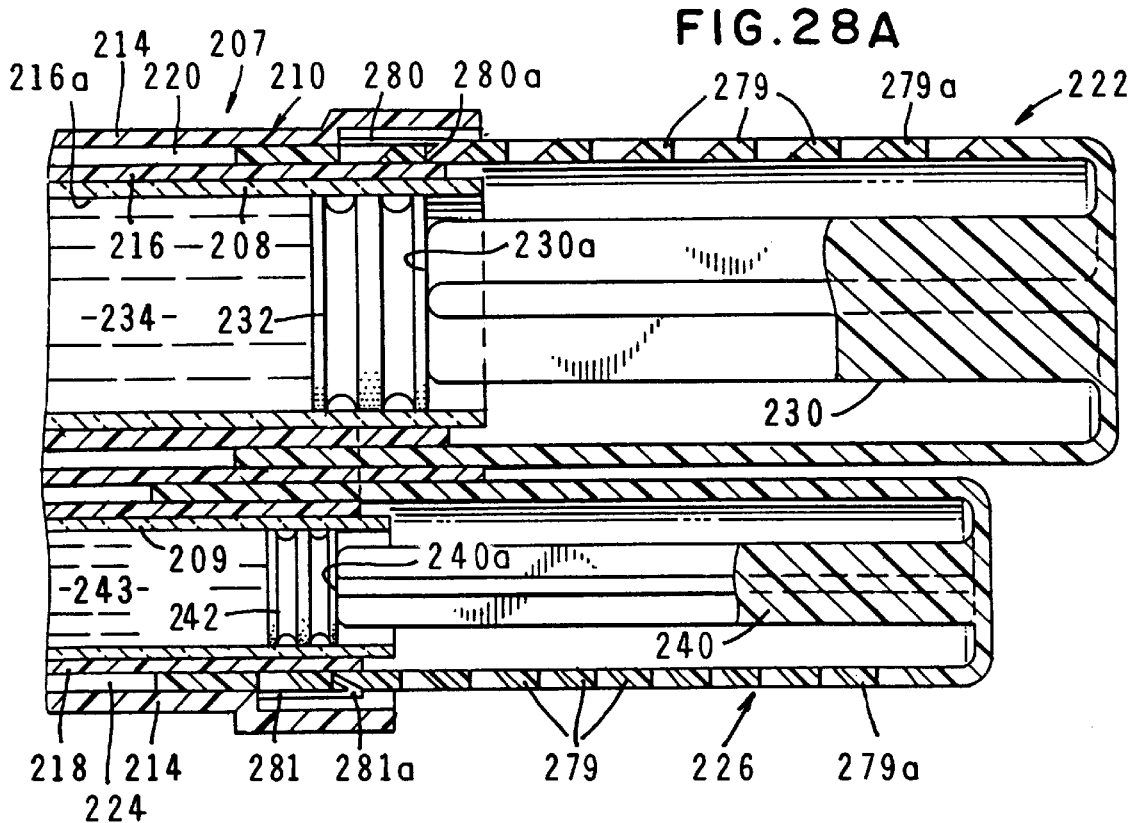
Figure 30:
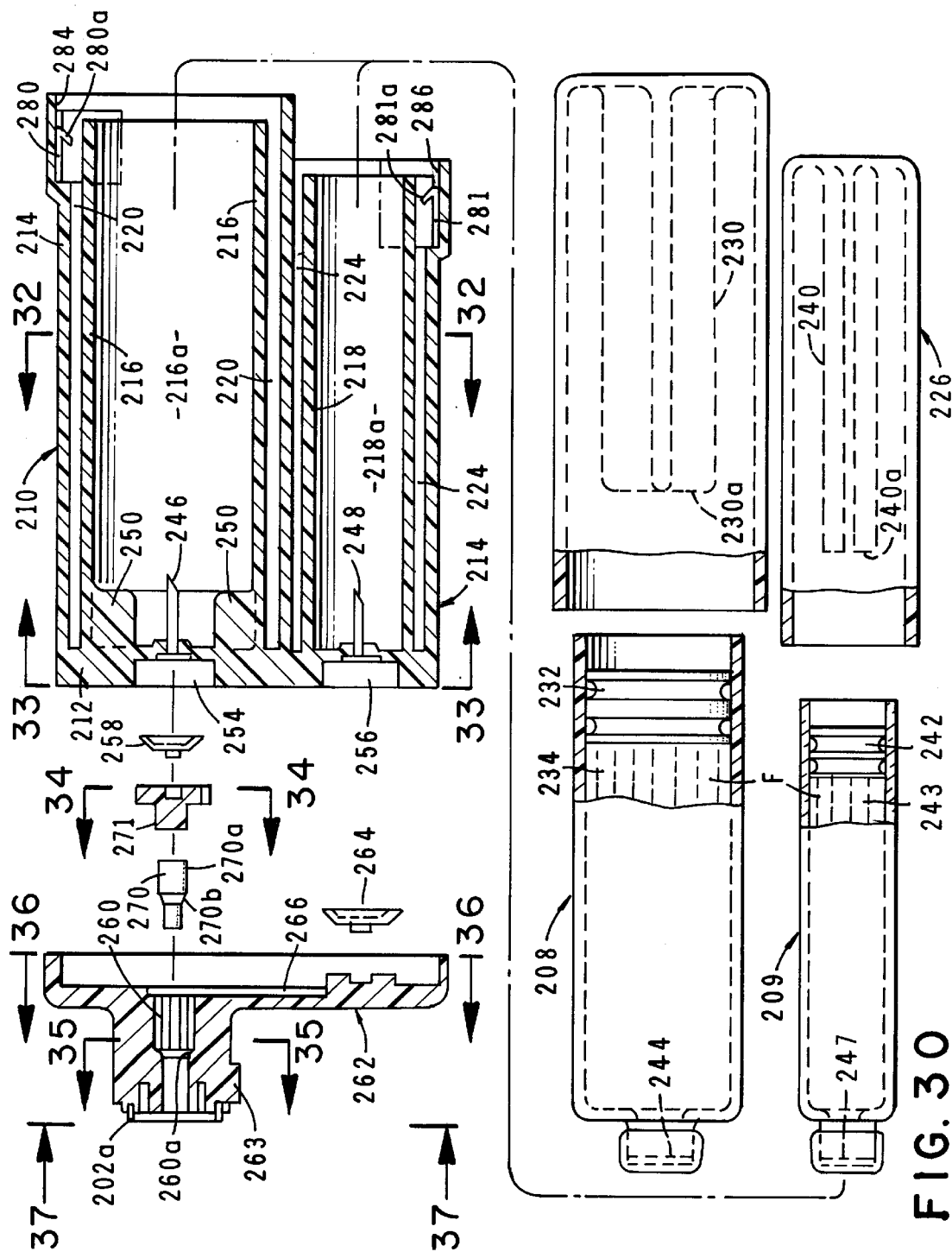
FIG. 30 is an exploded, cross-sectional view of the reservoir of the fill assembly of this latest form of the invention.

The major difference between the apparatus of this latest form of the invention and that shown in FIGS. 1 through 14 resides in the fact that the reservoir fill assembly, which is generally designated by the numeral 207, comprises multiple container assemblies 208 and 209 which are receivable within a differently configured adapter assembly 210 (FIG. 30). Referring particularly to FIGS. 28 and 28A, it is to be noted that body 212 of adapter subassembly 210 includes an outer wall 214 and radially spaced apart inner, generally cylindrically shaped walls 216 and 218 (FIG. 32).

Walls 214 and 216 define therebetween an elongated annular space 220 within which a first sleeve component 222 is telescopically received (FIG. 28A). Similarly, walls 214 and 218 define therebetween an elongated annular space 224 within which a second sleeve component 226 is received. As shown in FIG. 28, container assembly 208 is closely receivable with a chamber 216*a* formed internally of wall 216 of the adapter subassembly and can be urged forwardly of chamber 216*a* by inward telescopic movement of sleeve 222 into space 220. As was the case in the earlier described embodiments, the inboard end 230*a* of pusher rod 230 engages a first plunger 232 and urges it inwardly of first container reservoir 234 as sleeve 222 is moved inwardly of annular space 220 (FIG. 28A). In a similar fashion, container assembly 209 is closely receivable within a chamber 218*a* formed internally of wall 218 and can be urged forwardly of chamber 218*a* by inward telescopic movement of sleeve 226 into space 224. During mating of the second container assembly with the adapter assembly, the inboard end 240*a* of a pusher rod 240 engages a second plunger 242 and urges it inwardly of second container reservoir 243 as sleeve 226 is moved inwardly of annular space 224 (FIG. 28A).

During the initial mating of sleeves 222 and 226 with adapter subassembly 210, the resistance of the fluid within the containers of the container assemblies or vial cartridges 208 and 209 will resist movement of plungers 232 and 242 inwardly of their respective reservoirs so as to cause the vial cartridges to initially move inwardly of their respective chambers to a position wherein a septum 244 of container assembly 208 is engaged by a first cannula 246 of the adapter subassembly and a septum 247 of container assembly 209 is engaged by a second cannula 248 of the adapter subassembly. As before, guide ribs 250 formed interiorly of chamber 216*a*, guide the neck portion of vial assembly 208 toward cannula 246. Similarly, the interior surface of wall 218 of chamber 218*a* guides the neck position of vial assembly 209 toward cannula 248. A continued inward force on sleeves 222 and 226 will cause cannulas 246 and 248 to pierce their respective septums 244 and 247 in the manner shown in FIG. 28, thereby opening fluid communication between the reservoirs of the vial assemblies 208 and 209 and the internal fluid passageways of cannulas 246 and 248.

Once each of the septums has been pierced, the pusher rods of the pusher sleeves 222 and 226 will urge plungers 232 and 242 forwardly of their respective reservoirs causing the fluid within the reservoirs to flow into the central fluid passageways of cannulas 246 and 248 and, toward valve support chambers 254 and 256 formed in body 212 (FIG. 30). Disposed within chamber 254 is a first umbrella valve 258 which is of conventional construction. Umbrella valve 258 permits fluid flow from chamber 254 toward a fluid passageway 260 which is formed in a cover member 262 which is connected to adapter body 212 by any suitable means to form the construction shown in FIG. 28. However, valve 258 is constructed so as to block fluid flow in an opposite direction. Disposed within chamber 256 is a second umbrella valve 264 which permits fluid flow toward a fluid passageway 266 formed in cover 262 but blocks fluid flow in the opposite direction (see FIG. 28). As before, umbrella valves 258 and 264 comprise portions of the fill flow control means of the invention.

Formed within passageway 260 which is in communication with passageway 266 is a valve seat 260*a* (FIG. 30) and a plurality of circumferentially spaced fluid flow grooves 260*b* (FIG. 35). Disposed within passageway 260 is a valve means shown here as a check valve 270 for permitting fluid flow from cannula 246 and fluid passageway 260 toward the fluid reservoir of the dispenser component 14, and preventing fluid flow from assembly until mated with the fluid dispenser. Located between check valve 270 and umbrella valve 258 is a valve retainer member 271 which maintains the umbrella valve in position. Check valve 270, which is of conventional construction, includes a body portion 270*a* and a seat portion 270*b* which sealably engages seat 260*a* when valve 270 is in a closed position (FIG. 30). Valve 270 also forms a part of the fill flow control means of the invention for controlling the flow of fluid toward the dispenser component.

It is to be understood that container assemblies 208 and 209 can be filled with various fluids including a diluent as well as a wide variety of beneficial agents. Accordingly, following interconnection of the fill assembly with the dispenser component in the manner previously described, the multi-vial reservoir fill assembly of this latest form of the invention can advantageously be used to sequentially fill, totally fill, or partially fill, the reservoir of the fluid dispenser with fluids contained within the container assemblies for sequential delivery to the patient. Alternatively, the fill assembly can be used to simultaneously fill the fluid dispenser with the fluids contained within container assemblies 208 and 209 thereby creating a fluid mixture which can be delivered to the patient over a predetermined period of time.

Figure 37:
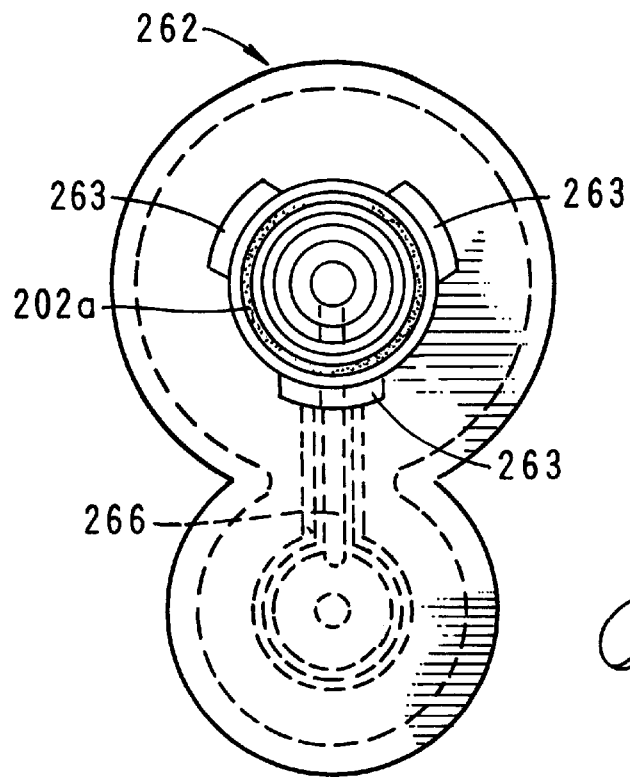
FIG. 37 is a view taken along lines 37—37 of FIG. 30.
Figure 38:
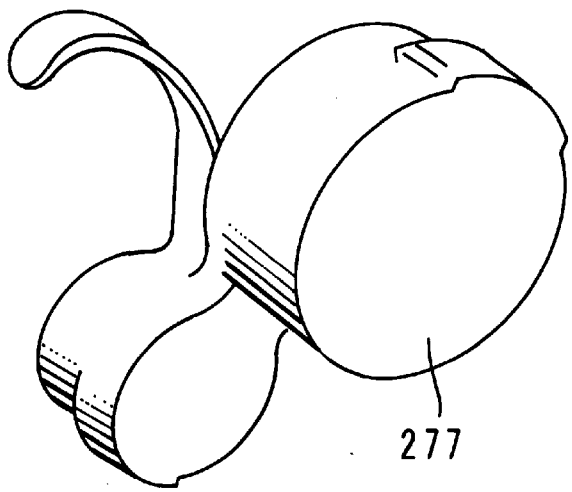
FIG. 38 is a generally perspective view of the closure cap embodiment of the present component of the invention for closing one end of the adapter subassembly.

Referring to FIGS. 30 and 37, it is to be noted that cover 262 is provided with locking tabs 263 which mate in bayonet locking fashion with slots 26c formed in end plate 26 of the dispenser component 14. Prior to use of the adapter subassembly, the open ends thereof are closed by a tearaway caps 277 of the character shown in FIG. 38.

Figure 29A:
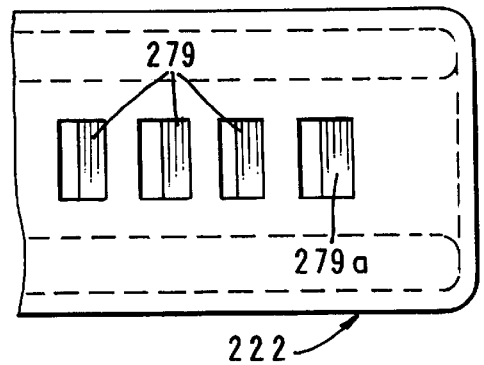
FIG. 29A is a fragmentary top plan view of a portion of one of the pusher sleeves of the apparatus shown in FIG. 28A.
Figure 29B:
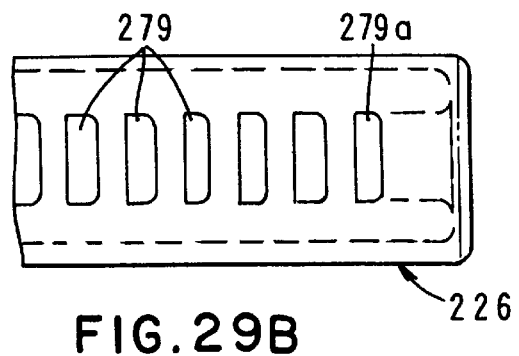
FIG. 29B is a fragmentary top plan view of a portion of the other pusher sleeve of the apparatus shown in FIG. 28A.

Turning particularly to FIGS. 29A, and 29B, it is to be noted that pusher sleeves 222 and 226 are provided with a plurality of longitudinally spaced, upstanding teeth 279 which form a part of the locking means of the invention for locking sleeves 222 and 226 to the adapter assembly after the filling of the reservoir of the fluid dispenser. As the sleeves are inserted into annular spaces 220 and 224, teeth 279 will slide under an inwardly extending tab 280a provided on locking clip 280 and under a tab 281a provided on clip 281 which is of the general configuration shown in FIGS. 30 and 31 and which also form a part of the locking means of the invention. Clips 280 and 281 are carried within reliefs 284 and 286 formed in the adapter assembly in the manner shown in FIG. 30. When the two sleeves are fully inserted into their respective annular spaces, tabs 280a and 281a formed on clips 280 and 281 will lockably engage rearward most tooth 279a on the sleeves thereby preventing separation of the sleeves from the adapter assembly.

As before, following the filling step, the adapter assembly can be disconnected from the dispenser unit and the closure cap 277 is once again placed over the adapter subassembly to maintain the subassembly in a protected, substantially sterile condition.

Figure 39:
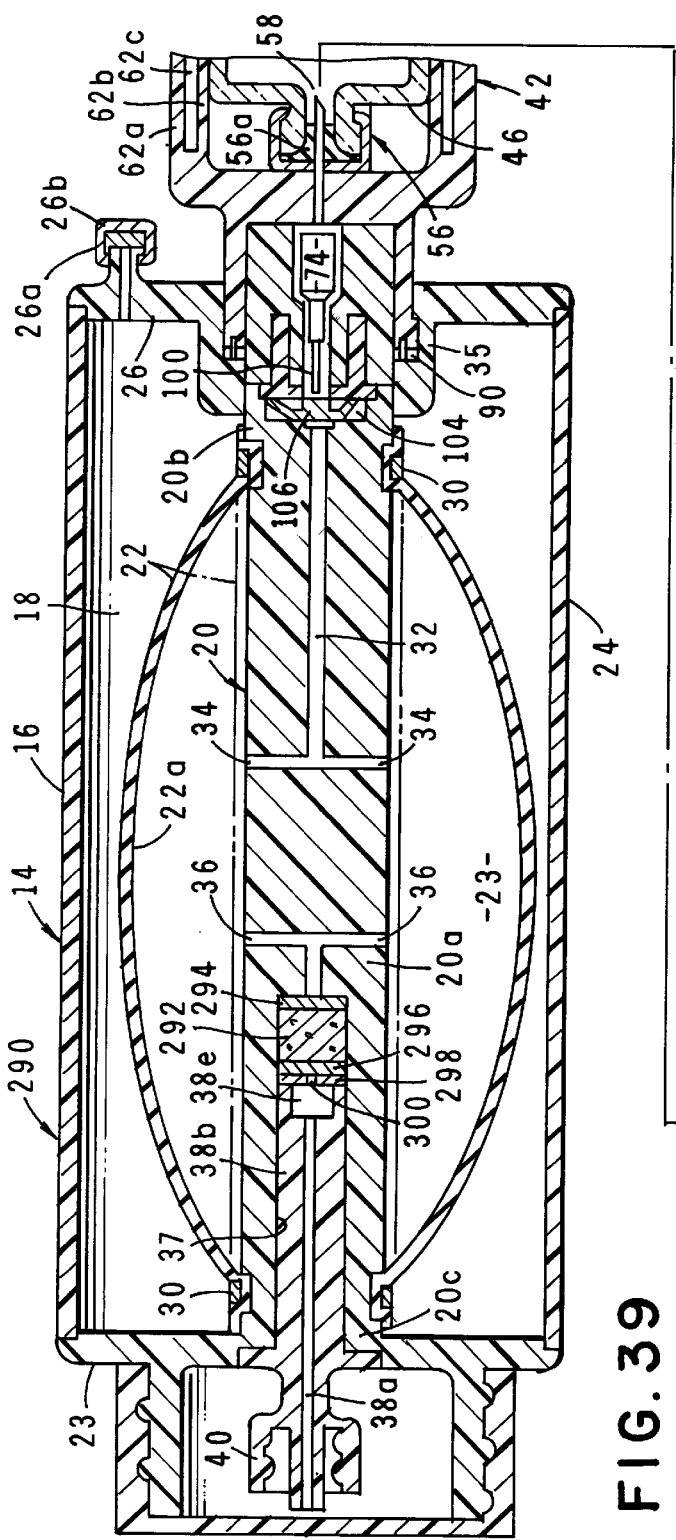
FIG. 39 is a partly cross-sectional, side-elevational view similar to FIG. 1 but showing an alternate form of the fluid flow control means.
Figure 40:
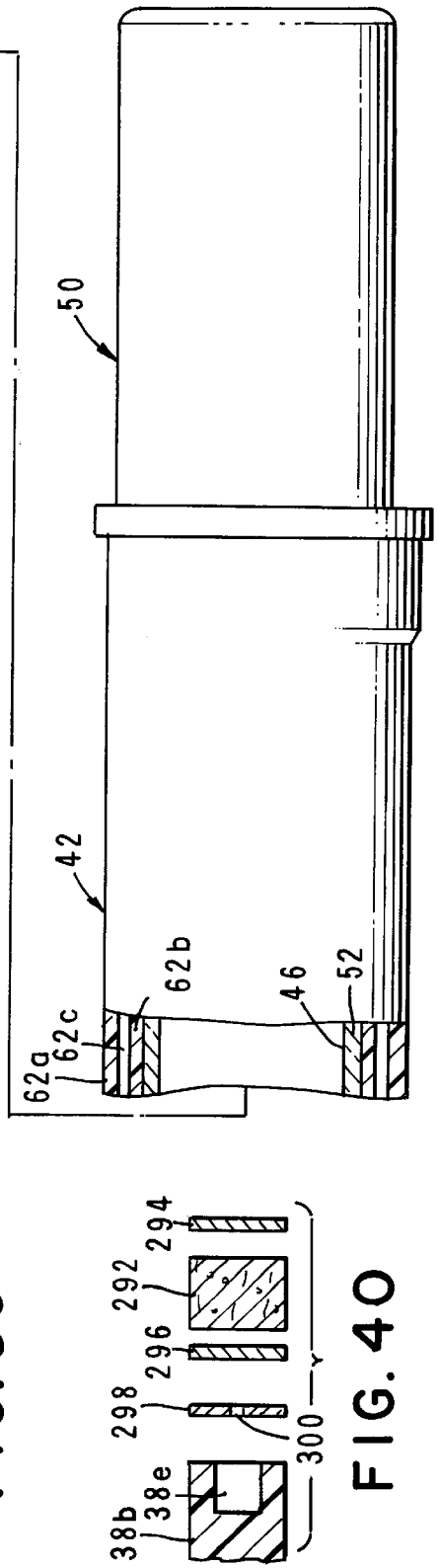
FIG. 40 is an exploded, cross-sectional view of the flow control means shown in FIG. 39.

Referring to FIGS. 39 and 40 another embodiment of the invention in there shown and generally designated by the numeral 290. This latest form of the invention is identical to that shown in FIGS. 1 through 14 save for the dispenser flow control means and like numerals are used to identify like components. As before, the fluid dispenser component, comprises an elongated housing 16 having an internal chamber 18, a support assembly 20 disposed within internal chamber 18, and extending longitudinally of the housing 16 and a generally cylindrically shaped, elongated elastomeric member 22. Elastomeric member 22 cooperates with support assembly 20 to define a fluid reservoir 23, the outer boundary of which is defined by the distended elastomeric member 22.

As shown in FIG. 39, support assembly 20 has a first end portion 20b having a fluid inlet 32 and fluid outlets 34. Fluid inlet 32 is accessible via dispenser connector means, generally designated as 35, to which the reservoir fill component of the apparatus can be operably connected. Support assembly 20 also includes a second end portion 20c having inlet fluid passageway 36 and an elongated internal chamber 37. Received within chamber 37 is a two-stage dispenser flow control means of a slightly different character from that previously described.

More particularly, the flow control means here comprises, in addition to the previously discussed valve means, which includes valve 74, a porous member 292, such as a porous frit formed from stainless steel, teflon, polyetheretherketone, or a ceramic. Member 292 is disposed within chamber 37 and has at either end thereof filters 294 and 296. Disposed between filter 296 and the inboard end of connector insert 38b is a wafer like element 298 having a central, laser drilled opening or microbore 300 which precisely controls fluid flow toward a counterbore 38e formed in passageway 38a (see also FIG. 40). Element 298 is preferably constructed from materials such as plastic films including polyester material. Element 298 can be constructed from a very thin film material, (for example, 0.010 to 0.030 inches) of a polyamide film sold by duPont under the name and style KAPTON. Filters 294 and 296, on the other hand, are preferably constructed from materials such as polysolfone and polypropylene, but other porous materials can also be used.

Turning next to FIGS. 41 and 41A, still another form of the invention is there shown and generally designated by the numeral 302. This latest form of the invention is also identical to that shown in FIGS. 1 through 14 save for the single-stage dispenser flow control means, and like numerals are used to identify like components.

The dispenser flow control means in this latest embodiment comprises, in addition to the previously discussed valve means, which includes valve 74, a filter 304 and a wafer-like element 306 which is disposed between filter 304 and the inboard end of connector insert 38c. Element 306 is similar in construction to element 298 and is provided with a very small central laser drilled microbore 308 which precisely controls fluid flow toward counterbore 38e and passageway 38a.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for use in infusing medicinal fluid into a patient at a controlled rate comprising:
   (a) a fluid dispenser comprising:
      (i) an elongate housing having walls defining an internal chamber;
      (ii) a support connected to said housing, said support being disposed within said internal chamber and having a dispenser connector and a fluid inlet and a fluid outlet; and
      (iii) an elongate tubular shaped elastomeric member connected proximate its ends to said support, said elastomeric member having a central portion disposed within said internal chamber of said housing and overlaying said fluid inlet and said fluid outlet of said support, said central portion of said elastomeric member being distendable by fluid flowing through said fluid inlet of said support from a first position in proximity with said support to a second position; and
   (b) a reservoir fill assembly interconnectable with said fluid dispenser for filling said fluid reservoir thereof, said reservoir fill assembly comprising:
      (i) a container subassembly including a container having a fluid chamber; closure means for sealably closing said first open end of said container; and a plunger movable relative to said container from a first location to a second, spaced-apart location;

(ii) an adapter subassembly comprising a hollow housing having a first open end for receiving a part of said container of said container assembly and a second end, said hollow housing further including an adapter connector mateably interconnectable with said dispenser connector for removably interconnecting said adapter subassembly with said fluid dispenser; and (iii) an adapter sleeve interconnectable with said adapter subassembly for movement between first and second positions, said adapter sleeve including pusher means for engagement with said plunger of said container subassembly to move said plunger between said first and second locations upon movement of said adapter sleeve toward said second position.

2. An apparatus as defined in claim 1 in which said fluid dispenser further includes dispenser flow control means for controlling fluid flow from said fluid outlet of said support.

3. An apparatus as defined in claim 1 in which said adapter subassembly includes fill flow control means including valve means for controlling fluid flow from said container subassembly toward said fluid inlet of said support.

4. An apparatus as defined in claim 3 in which said valve means comprises a valve seat formed in said adapter connector and a valve member disposed within said adapter connector for movement between a first position in sealing engagement with said valve seat to a second position spaced apart from said valve seat.

5. An apparatus for use in infusing medicinal fluid into a patient at a controlled rate comprising:
(a) a fluid dispenser comprising:
(i) an elongate housing having walls defining an internal chamber;
(ii) a support connected to said housing, said support being disposed within said internal chamber and having a dispenser connector and a fluid inlet and a fluid outlet;
(iii) an elastomeric member connected to said support, said elastomeric member having a central portion disposed within said internal chamber of said housing and overlaying said fluid inlet and said fluid outlet of said support said central portion of said elastomeric member being distendable by fluid flowing through said fluid inlet of said support from a first position in proximity with said support to a second position; and
(iv) dispenser flow control means for controlling fluid flow toward said fluid outlet; and
(b) a reservoir fill assembly interconnectable with said fluid dispenser for filling said fluid reservoir thereof, said reservoir fill assembly comprising:
(i) a container subassembly including a container having a body portion, a fluid chamber, and first and second open ends; a pierceable septum for sealably closing said first open end of said container; and a plunger telescopically movable within said container from a first location proximate said second open end to a second, spaced-apart location;
(ii) an adapter subassembly comprising a hollow housing having a cannula for piercing said pierceable septum; an annular passageway; a first open end for telescopically receiving at least a part of said body portion of said container of said container assembly;

and a second end, said hollow housing further including an adapter connector mateably interconnectable with said dispenser connector for removably interconnecting said adapter subassembly with said fluid dispenser; and (iii) an adapter sleeve interconnectable with said adapter subassembly for movement between a first position and a second position, said adapter sleeve including pusher means for engagement with said plunger of said container subassembly to move said plunger within said container between said first and second locations as said adapter sleeve moves toward said second position.

6. An apparatus as defined in claim 5 in which said dispenser flow control means comprises a permeable porous member.

7. An apparatus as defined in claim 5 in which said support is provided with an internal chamber and in which said flow control means comprises a porous member disposed within said internal chamber.

8. An apparatus as defined in claim 5 in which said adapter subassembly includes fill flow control means including valve means for controlling fluid flow from said container subassembly toward said fluid inlet of said support.

9. An apparatus as defined in claim 8 in which said valve comprises a valve member carried by said adapter subassembly for movement between a first position and a second position.

10. An apparatus as defined in claim 8 in which said closure means of said container subassembly comprises an elastomeric septum and in which said fill flow control means comprises a hollow cannula.

11. An apparatus as defined in claim 10 in which said fill flow control means comprises valve means in fluid communication with said hollow cannula.

12. An apparatus as defined in claim 10 in which said elastomeric septum comprises a non-corable material and in which said hollow cannula comprises a sharp-end cannula.

13. An apparatus as defined in claim 10 in which said elastomeric septum is slitted and in which said hollow cannula comprises a blunt-end cannula.

14. An apparatus as defined in claim 10 in which said closure means of said container subassembly further includes a clamping ring for crimping engagement with said container to hold said elastomeric septum in place.

15. An apparatus for use in infusing medicinal fluid into a patient at a controlled rate comprising:
(a) a fluid dispenser comprising:
(i) an elongate housing having walls defining an internal chamber;
(ii) a support connected to said housing, said support being disposed within said internal chamber and having a dispenser connector, a fluid inlet and a fluid outlet;
(iii) an elastomeric member connected to said support, said elastomeric member having a central portion disposed within said internal chamber of said housing and overlaying said fluid inlet and said fluid outlet of said support said central portion of said elastomeric member being distendable by fluid flowing through said fluid inlet of said support from a first position in proximity with said support to a second position; and
(iv) dispenser flow control means for controlling fluid flow toward said fluid outlet; and
(b) a reservoir fill assembly interconnectable with said fluid dispenser for filling said fluid reservoir thereof, said reservoir fill assembly comprising:

(i) a first container subassembly including a container having a body portion, a fluid chamber, and first and second open ends; an elastomeric septum for sealably closing said first open end of said container; and a plunger telescopically movable within said container from a first location proximate said second open end to a second, spaced-apart location;

(ii) an adapter subassembly comprising a hollow housing having a first annular passageway and a first open end for telescopically receiving at least a part of said body portion of said container of said container assembly and a second end portion including a hollow cannula adapted to pierce said elastomeric septum, said hollow housing further including an adapter connector mateably interconnectable with said dispenser connected for removably interconnecting said adapter subassembly with said fluid dispenser; and (iii) an adapter sleeve interconnectable with said adapter subassembly, said adapter sleeve including pusher means for engagement with said plunger of said container of said first container subassembly to move said plunger within said container between said first and second locations.

16. An apparatus as defined in claim 15 in which said dispenser flow control means comprises a porous member.

17. An apparatus as defined in claim 15 in which said dispenser flow control means comprises a filter and a wafer-like element having a microbore formed therein.

18. An apparatus as defined in claim 15 in which said dispenser flow control means comprises a two-stage, flow control including a filter, a porous member, and a thin element having a microbore formed centrally thereof.

19. An apparatus as defined in claim 15 in which said adapter subassembly further includes valve means for controlling fluid flow from said first container subassembly toward said fluid inlet of said support.

20. An apparatus as defined in claim 15 in which said hollow cannula comprises a blunt end cannula and in which said elastomeric septum includes a slit body portion.

21. An apparatus as defined in claim 15 in which said reservoir fill assembly further comprises a second container subassembly and in which said adapter subassembly comprises a hollow housing having a second annular passageway for receiving at least a portion of said second container subassembly.

22. An apparatus as defined in claim 21 further including a second adapter sleeve interconnectable with said adapter subassembly.

23. An apparatus as defined in claim 22 in which said reservoir fill assembly includes locking means for locking said first and second adapter sleeves to said adapter subassembly.

24. An apparatus for use in infusing medicinal fluid into a patient at a controlled rate comprising:
(a) a fluid dispenser comprising:
(i) an elongate housing having walls defining an internal chamber;
(ii) a support connected to said housing, said support being disposed within said internal chamber and having a dispenser connector and a fluid inlet and a fluid outlet;
(iii) an elongate tubular shaped elastomeric member connected proximate its ends to said support, said elastomeric member having a central portion disposed within said internal chamber of said housing and overlaying said fluid inlet and said fluid outlet of said support, said central portion of said elastomeric member being distendable by fluid flowing through said fluid inlet of said support from a first position in proximity with said support to a second position; and
(iv) dispenser flow control means for controlling fluid flow toward said fluid outlet of said support; and (b) a reservoir fill assembly interconnectable with said fluid dispenser for filling said fluid reservoir thereof, said reservoir fill assembly comprising:
(i) a container subassembly including a container having a body portion, a fluid chamber, and first and second open ends; a pierceable septum for sealably closing said first open end of said container and a plunger telescopically movable within said container from a first location proximate said second open end to a second, spaced-apart location;
(ii) an adapter subassembly comprising a hollow housing having an annular passageway and a first open end for telescopically receiving a part of said body portion of said container of said container subassembly and a second end provided with a hollow cannula for piercing said pierceable septum, said hollow housing further including an adapter connector mateably interconnectable with said dispenser connector of said base of said housing assembly for removably interconnecting said adapter subassembly with said fluid dispenser; and
(iii) an adapter sleeve telescopically receivable within said annular passageway of said hollow housing said sleeve subassembly including pusher means for engagement with said plunger to move said plunger within said container between said first and second locations.

25. A device as defined in claim 24 in which said dispenser flow control means comprises a porous member carried by said support of said fluid dispenser.

26. A device as defined in claim 24 in which said dispenser flow control means comprises a thin, wafer-like element having a microbore formed therein.

27. A device as defined in claim 24 in which said dispenser flow control means for controlling fluid flow from said fluid outlet port of said support comprises a hollow cannula.

28. A device as defined in claim 24 in which said dispenser flow rate control means comprises a hollow piercing cannula.

29. A device as defined in claim 24 in which said dispenser flow rate control means comprises a blunt-end hollow cannula.

30. A device as defined in claim 24 in which said dispenser flow rate control means comprises a laser drilled wafer and a backup flow rate control means comprising a porous member.

31. A device as defined in claim 24 in which said reservoir fill assembly further includes fill flow control means, said fill flow control means comprising a valve member carried by said hollow housing.

32. A device as defined in claim 31 in which said fill flow control means comprises a septum carried by said adapter subassembly.

33. A device as defined in claim 31 in which said fill flow control means comprises a slit septum carried by said adapter subassembly.

34. An apparatus for use in infusing medicinal fluid into a patient at a controlled rate comprising:
(a) a fluid dispenser comprising:
(i) an elongate housing having walls defining an internal chamber;

(ii) a support connected to said housing, said support being disposed within said internal chamber and having a dispenser connector and a fluid inlet and a fluid outlet; and (iii) an elongate tubular shaped elastomeric member connected proximate its ends to said support, said elastomeric member having a central portion disposed within said internal chamber of said housing and overlaying said fluid inlet and said fluid outlet of said support, said central portion of said elastomeric member being distendable by fluid flowing through said fluid inlet of said support from a first position in proximity with said support to a second position; and (b) a reservoir fill assembly interconnectable with said fluid dispenser for filling said fluid reservoir thereof, said reservoir fill assembly comprising:

(i) a container subassembly, including a container having a fluid chamber and a plunger movable relative to said fluid chamber from a first location to a second spaced-apart location;

(ii) an adapter subassembly comprising a hollow housing having a fluid outlet, an outer wall and an inner wall defining therebetween a generally annular shaped passageway for containing a fluid, said inner wall having a first open end for telescopically receiving at least a part of said container of said container subassembly and a second end, said hollow housing further including connector means for connecting said adapter subassembly with the fluid dispenser; and (iii) an adapter sleeve mateable with said adapter subassembly including means for engagement with said plunger of said container subassembly to move said plunger between said first and second locations and further including a generally ring shaped member sealably received within said annular shaped passageway for urging fluid contained within said passageway outwardly thereof toward said fluid outlet of said hollow housing.

35. An apparatus as defined in claim 34 in which said inner wall of said adapter subassembly is generally circular in cross section and in which said outer wall thereof is generally elliptical in cross section.

36. An apparatus as defined in claim 34 in which said container subassembly includes a pierceable septum and in which said hollow housing of said adapter subassembly includes a hollow cannula for piercing said septum.

37. An apparatus as defined in claim 34 in which said adapter subassembly includes valve means for controlling fluid flow toward said fluid outlet thereof.

38. An apparatus as defined in claim 34 in which the fluid dispenser includes a septum and in which said adapter subassembly of said reservoir fill assembly includes a second hollow cannula for piercing a septum of the fluid dispenser.

39. An apparatus as defined in claim 34 in which said fluid dispenser includes a hollow cannula and in which said adapter subassembly of said reservoir fill assembly includes a septum pierceable by the hollow cannula of the fluid dispenser.

40. A reservoir fill assembly as defined in claim 39 in which said septum of said adapter subassembly comprises a slit septum.

41. An apparatus for use in infusing medicinal fluid into a patient at a controlled rate comprising:

(a) a fluid dispenser comprising:

(i) an elongate housing having walls defining an internal chamber;

(ii) a support connected to said housing, said support being disposed within said internal chamber and having a dispenser connector and a fluid inlet and a fluid outlet; and (iii) an elongate tubular shaped elastomeric member connected proximate its ends to said support, said elastomeric member having a central portion disposed within said internal chamber of said housing and overlaying said fluid inlet and said fluid outlet of said support, said central portion of said elastomeric member being distendable by fluid flowing through said fluid inlet of said support from a first position in proximity with said support to a second position; and (b) a reservoir fill assembly interconnectable with said fluid dispenser for filling said fluid reservoir thereof, said reservoir fill assembly comprising:

(i) a container subassembly including first and second containers each having a fluid chamber and a plunger movable relative to said fluid chamber from a first location to a second, spaced-apart location;

(ii) an adapter subassembly comprising a hollow housing having a fluid outlet, an outer wall and further including:

a. a first inner wall defining, in conjunction with said outer wall, a first generally annular-shaped passageway, said first inner wall having a first open end for telescopically receiving at least a portion of said first container of said container subassembly; and b. a second inner wall defining in conjunction with said outer wall a second generally annular shaped passageway, said second inner wall having a first open end for telescopically receiving at least a portion of said second container of said container subassembly;

(iii) an adapter sleeve mateable with said adapter subassembly including first means for engagement with said plunger of said first container of said container subassembly to move said plunger between said first and second locations and further including second means for engagement with said plunger of said second container of said container subassembly to move said plunger between said first and second locations.

* * * * *